(12) United States Patent
Ignatious

(10) Patent No.: US 7,196,145 B2
(45) Date of Patent: Mar. 27, 2007

(54) HETEROFUNCTIONAL COPOLYMERS OF GLYCEROL AND POLYETHYLENE GLYCOL, THEIR CONJUGATES AND COMPOSITIONS

(75) Inventor: Francis Ignatious, King of Prussia, PA (US)

(73) Assignee: SmithKline Beecham Corporation, Philadephia, PA (US)

( * ) Notice: Subject to any disclaimer, the term of this patent is extended or adjusted under 35 U.S.C. 154(b) by 21 days.

(21) Appl. No.: 10/926,215

(22) Filed: Aug. 25, 2004

(65) Prior Publication Data

US 2005/0048650 A1    Mar. 3, 2005

(51) Int. Cl.
C08G 65/02    (2006.01)
C08G 65/26    (2006.01)
A61K 9/00     (2006.01)

(52) U.S. Cl. .................... 525/523; 528/408; 528/421; 427/2.14; 424/417

(58) Field of Classification Search ............ None
See application file for complete search history.

(56) References Cited

U.S. PATENT DOCUMENTS

| | | | |
|---|---|---|---|
| 4,737,323 A | 4/1988 | Martin et al. | |
| 4,762,915 A | 8/1988 | Kung et al. | |
| 5,013,556 A | 5/1991 | Woodle et al. | |
| 5,077,056 A | 12/1991 | Bally et al. | |
| 5,395,619 A | 3/1995 | Zalipsky et al. | |
| 5,631,018 A | 5/1997 | Zalipsky et al. | |
| 5,855,866 A | 1/1999 | Thorpe et al. | |
| 2003/0027929 A1 | 2/2003 | Varshney et al. | |
| 2003/0092879 A1* | 5/2003 | Sunder et al. | 528/403 |
| 2003/0120022 A1* | 6/2003 | Sunder et al. | 528/95 |

FOREIGN PATENT DOCUMENTS

| | | |
|---|---|---|
| EP | 0688207 | 1/1998 |
| WO | WO 98/17256 | 4/1998 |
| WO | WO 99/55367 | 10/1999 |
| WO | WO 00/23052 | 4/2000 |

OTHER PUBLICATIONS

Hennequin, et al., *Journal of Medicinal Chemistry*, vol. 39 pp. 695-704 (1996).
Kono, et al., *Biochemica et Biophysica Acta*, vol. 1325 pp. 143-154 (1997).
Kono, et al., *Gene Therapy*, vol. 8 pp. 5-12 (2001).
Kono, et al., *Journal of Controlled Release*, vol. 68 pp. 225-235 (2000).
Moghimi, et al., *Pharmacol. Rev.*, vol. 53(2) pp. 283-318 (2001).
Riou, et al., *Molecular Pharmacology*, vol. 40(5) pp. 699-706 (1991).
Storm, et al., *Adv. Drug Delivery Rev.*, vol. 17(1) pp. 31-48 (1995).
Sun, et al., *Journal of Medicinal Chemistry*, vol. 43 pp. 2655-2663 (2000).
Sunder, et al., *Angewandte Chemie International Edition*, vol. 38(23) pp. 3552-3555 (1999).
Szoka, et al., *Ann Rev Biophys Bioeng*, vol. 9 p. 467 (1980).
Utsugi et al., *Japanese Journal of Cancer Research*, vol. 88(10) pp. 992-1002 (1997).
Zalipsky, et al., *Eur Polymer Journal*, vol. 19(12) pp. 1177-1183 (1983).
Bridges, et al., *Journal of Medicinal Chemistry*, vol. 39 pp. 267-276 (1996).
Dimitrov, et al., *Polymer*, vol. 43(25) pp. 7171-7178 (2002).
Haran, et al., *Biochemica et Biophysica Acta*, vol. 1151 pp. 201-215 (1993).
Kanzawa, et al., *Cancer Research*, vol. 55(13) pp. 2806-2813 (1995).
Kunimoto, et al., *J. Pharmacobio-Dyn.*, vol. 10(3) pp. 148-151 (1987).
Lasic, et al., *Bioelectrochemistry & Bioenergetics*, vol. 48 (2) p. 490 (1999).
Lasic, *Trends in Biotechnology*, vol. 16(7) ogs 307-321 (1998).
Laverman, et al. *J. Liposomes Res*, vol. 10(2 & 3) pp. 117-129 (2000).
Mayer, et al., *Biochemica et Biophysica Acta*, vol. 858(1) pp. 161-168 (1986).
Rothenberg, *Annals of Oncology*, vol. 8(9) pp. 837-855 (1997).
Zalipsky, *Advanced Drug Delivery Review*, vol. 16 pp. 157-182 (1995).
Zhu, et al., *Cancer Chemother Pharmacol*, vol. 39 pp. 138-142 (1996).
Sawada, et al., *Chem Pharm Bull*, vol. 41(2) pp. 310-313 (1993).
Zhang, et al., *Polymeric Biomaterials*, 2$^{nd}$ Edition pp. 783-821 (2002).

* cited by examiner

*Primary Examiner*—Michael J. Feely
(74) *Attorney, Agent, or Firm*—Dara L. Dinner; Stephen Venetianer; Charles M. Kiuzig

(57) ABSTRACT

The present invention relates to heterofunctional copolymers of glycerol and polyethylene glycol, conjugates of these heterofunctional copolymers with bioactive agents, nanoparticles, hydrophobic polymers and/or lipids; and to compositions containing these conjugates.

51 Claims, 4 Drawing Sheets

Example 1

Example 2

Example 3

Figure 1:
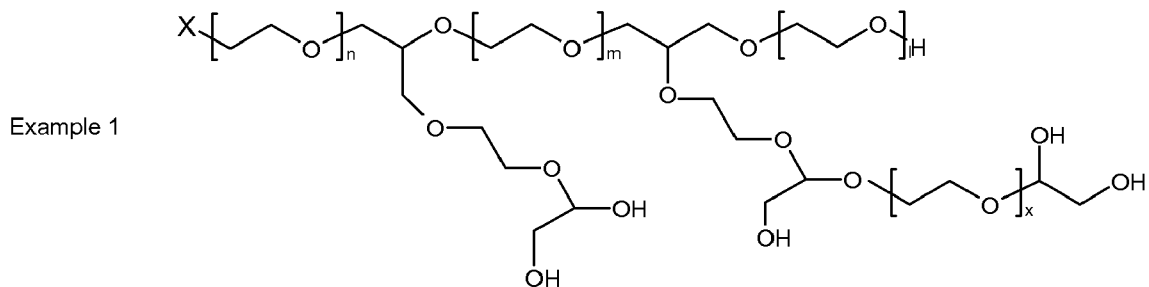
Figure 1:
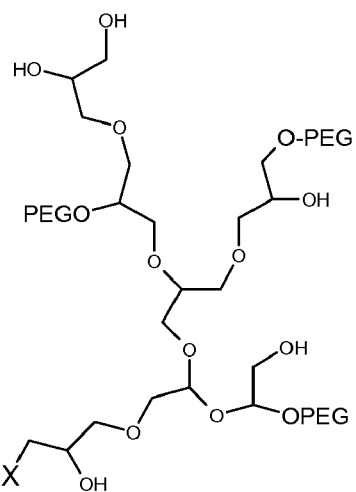
Figure 1:
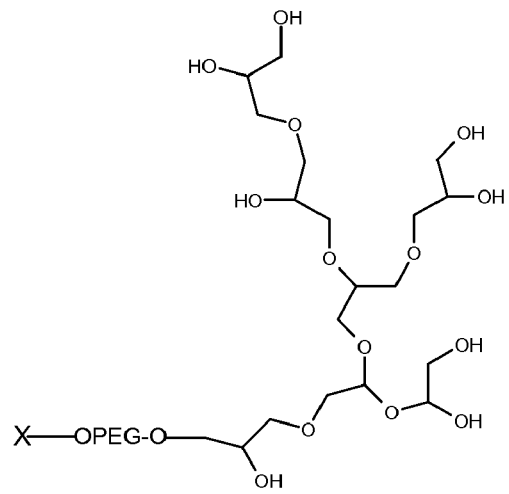

HETEROFUNCTIONAL COPOLYMERS OF GLYCEROL AND POLYETHYLENE GLYCOL, THEIR CONJUGATES AND COMPOSITIONS

FIELD OF THE INVENTION

The present invention relates to heterofunctional copolymers of glycerol and polyethylene glycol, conjugates of these heterofunctional copolymers with bioactive agents, nanoparticles, and lipids; and compositions containing these conjugates. These conjugates can provide extended circulating time in the human body compared to non-conjugated bioactive agents, nanoparticles and liposomes.

BACKGROUND OF THE INVENTION

Conjugation of water soluble polymers to bioactive agents and colloidal carrier systems such as nanoparticles, micelles, niosomes and liposomes, is used to prolong their circulation half-life and reduced toxicity in human body, which in turn provides superior efficacy, less dosing frequency and better patient compliance. The superior efficacy of polymer conjugated bioactive agents is demonstrated by several marketed products like PEG-Intron®, Neulasta®, Somavert®, Oncospar®, Adagen® and PEGASYS®, wherein polyethylene glycol, hereafter referred to as 'PEG' is conjugated to various protein therapeutics. These products exemplify the use of water soluble polymer conjugated to water soluble therapeutic proteins to prolong the circulation half life.

Conjugation of water soluble polymers to water insoluble bioactive agents, is being investigated to enhance the solubility of the water insoluble active. Examples of such systems under development are polyethylene glycol conjugated camptothecin, polyglutamic acid conjugated paclitaxel and polyhydroxymethacrylamide conjugated paclitaxel.

Water soluble polymers may be coupled to hydrophobic polymers in block architecture. These block copolymers spontaneously self assemble in aqueous medium to form polymeric micelles and nanoparticles. These polymeric micelles and nanoparticles, have a hydrophobic core and an outer hydrophilic shell around it. The hydrophobic inner core can incorporate water insoluble hydrophobic drugs by hydrophobic association. Therefore these polymeric micelles and nanoparticles can be used for drug delivery.

An important characteristics of polymer conjugated systems is its passive accumulation at tumour site by size effect, known as epr (enhanced permeability and retention) effect' due to the leaky nature of the tumor vasculature. This passive targeting is the mechanism of action of an anti-tumor agent, SMANCS, approved in Japan for liver cirrhosis. SMANCS consists of low molecular weight styrene maleic anhydride copolymer conjugated to neocarzinostatin through the anhydride groups present in the polymer. Although the molecular weight of SMANCS is about 16–17 kDa, it forms larger aggregates with serum albumin. The aggregated size of the conjugate, 80 kDa, is said to responsible for the spontaneous but passive accumulation of SMANCS at the tumor site.

The above described passive targeting mechanism is also demonstrated by nanoparticles and polymeric micelles having diameter less than 200 nm, provided they have a prolonged plasma circulation half life. Since the nanoparticles and polymeric micelles are inherently coated with a hydrophilic water soluble polymer, they are expected to enhance plasma circulation half life and hence passive accumulation at the tumor site. Unlike nanoparticles and polymeric micelles, liposomes do not inherently have a hydrophilic polymer coating to prevent uptake by Mononuclear Phagocyte System (MPS) and rapidly cleared from the circulation to organs rich in phagocytic cells, like liver, spleen and bone marrow.

Liposomes are small vesicles having one or more concentric lipid bilayers enclosing an aqueous space. Because of their structural versatility in terms of size, surface charge, lipid composition, bilayer fluidity and because of their ability to encapsulate almost every drug, their importance as drug delivery systems was readily appreciated. However, on intravenous injecting of liposomes, these are recognized as foreign particles by the Mononuclear Phagocyte System (MPS) and rapidly cleared from the circulation to organs rich in phagocytic cells, like liver, spleen and bone marrow.

Several possibilities to reduce this effect have been identified, such as decreasing the particle size of the liposomes and changing the surface charge of the liposomes. Another development relates to surface modification of the liposomes by the introduction of specific hydrophilic polymeric components on the liposomal surface, which groups reduce protein adsorption on the particle surface. Consequently such liposomes are protected against recognition by cells of the MPS and have a prolonged residence time in the general circulation. A well-known example of modification of the liposomal surface is the incorporation during the preparation of liposomal compositions of a lipid derivative of the hydrophilic polymer polyethylene glycol (PEG). Usually this hydrophilic polymer is terminus-modified with a hydrophobic moiety, which is the residue of a phosphatidyl ethanolamine derivative or a long-chain fatty acid. Polyethylene glycol per se is a rather stable polymer which is a repellent of protein adhesion and which is not subject to enzymatic or hydrolytic degradation under physiological conditions.

Good results with respect to extending plasma half life and diminishing accumulation into the organs rich in phagocytic cells have been obtained following intravenous administration of liposomes, having a PEG-grafted surface, to various animal species and also to human beings (Storm G., Belliot S. O., Daemen T. and Lasic. D. D.: Surface modification of nanoparticles to oppose uptake by the mononuclear phagocyte system in Adv. Drug Delivery Rev. 17, 31–48, (1995); Moghimi S. M., Hunter A. C. and Murray J. C.: Long-circulating and target-specific nanoparticles; theory to practice in Pharmacol. Rev. 53, 283–318, (2001)). Marketing approvals for such liposomal preparations, containing doxorubicin, have been obtained.

Until now the commercially available preparations based on PEG-liposomes are aqueous suspension preparations. It is well-known that the shelf life of liposomal aqueous suspension preparations in general and also of PEG-liposomes is rather limited. Several techniques how to remove the vehicle or continuous phase of such preparations are known, such as, spray-drying, diafiltration, rotational evaporation, and freeze-drying. Recently a freeze-drying method, which improved the long term shelf life of PEG-liposomes, containing the technetium-chelator hydrazino nicotinamide, was proposed (Layerman P., van Bloois L., Boerman O. C., Oyen W. J. G., Corstens F. H. M. and Storm G.: Lyophilisation of Tc-99m-HYNIC labelled PEG-liposomes in J. Liposome Res. 10(2&3), page 117–129 (2000)), but further investigations into the results and applicability of this technique to liposomal preparations are required.

The disadvantages inherent to the use of polyethylene glycol urged investigators to look for alternative polymers. Many polymers have been suggested as suitable candidates for derivatizing them with (vesicle-forming) lipids for incorporation into liposomes (see e.g. EP-0688207). The hydrophilic water soluble polymers poly(vinylpyrrolidone), poly (acryloylmorpholine), poly(2-(m)ethyl-2-oxazoline, polyacrylamide and polyglycerol have shown to prolong the circulation time of liposomes after intravenous administration to a certain extent. However, until now such lipid polymer conjugates have not been applied in commercially available drug preparations, mainly because they have not shown any advantages over the known lipid-PEG-conjugates.

Therefore there still is a need to find a polymer which can be derivatized with a lipid to enable incorporation into colloidal carrier compositions, such as liposomes, such polymer having long-circulating properties.

DETAILED DRAWINGS OF THE INVENTION

FIG. 1 discloses three examples of random or branched copolymers. Example 1 shows a random copolymer of glycidol and ethylene oxide. Example 2 shows a block copolymer containing branched polyglycidol, to which polyethylene oxide blocks are attached. Example 3 shows a block copolymer which a different architecture than Example 2.

Figure 2:
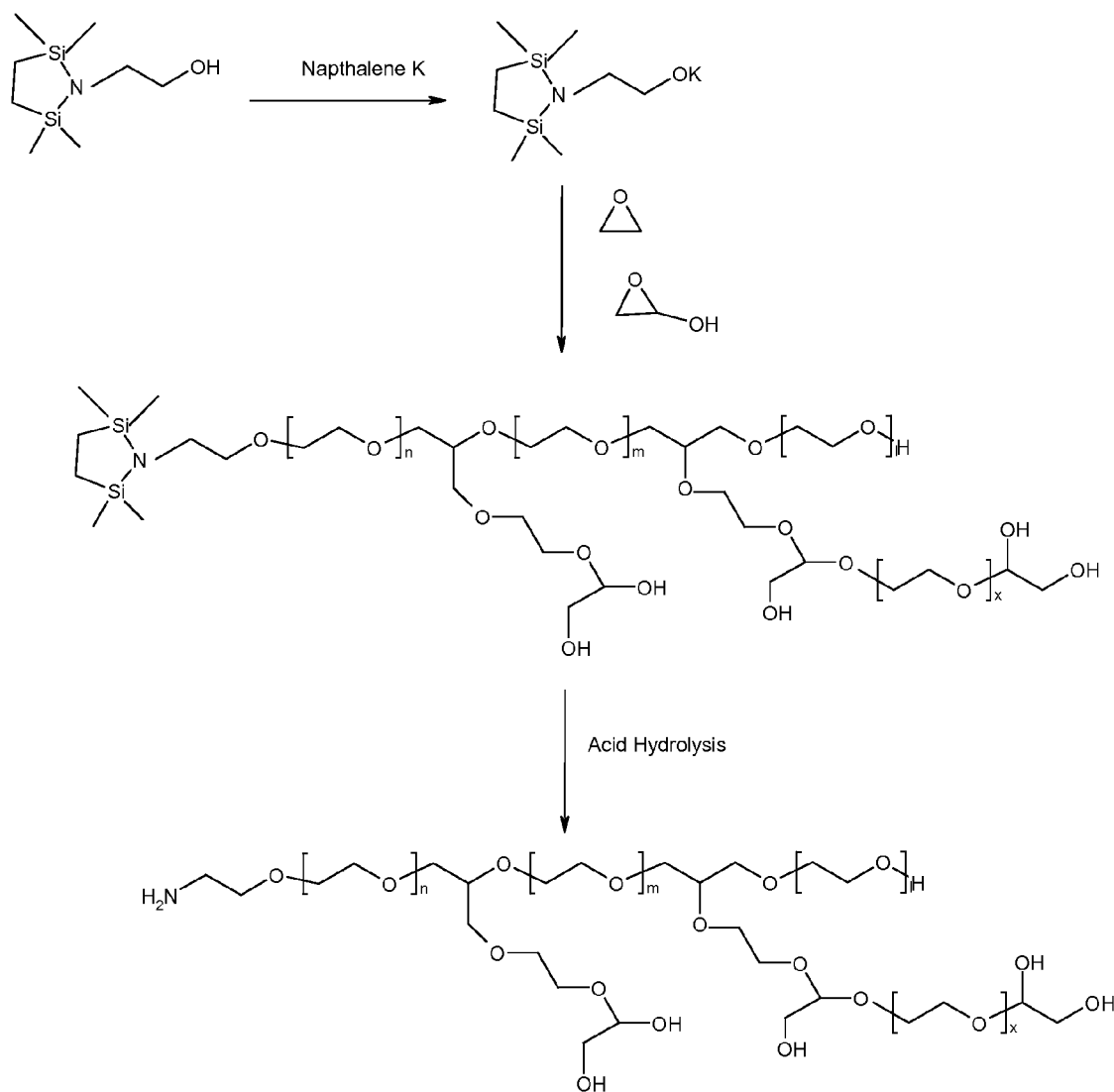

FIG. 2 discloses a schematic representation of the polymerization of ethylene oxide using potassium bis(trimethylsilyl)amide.

Figure 3:
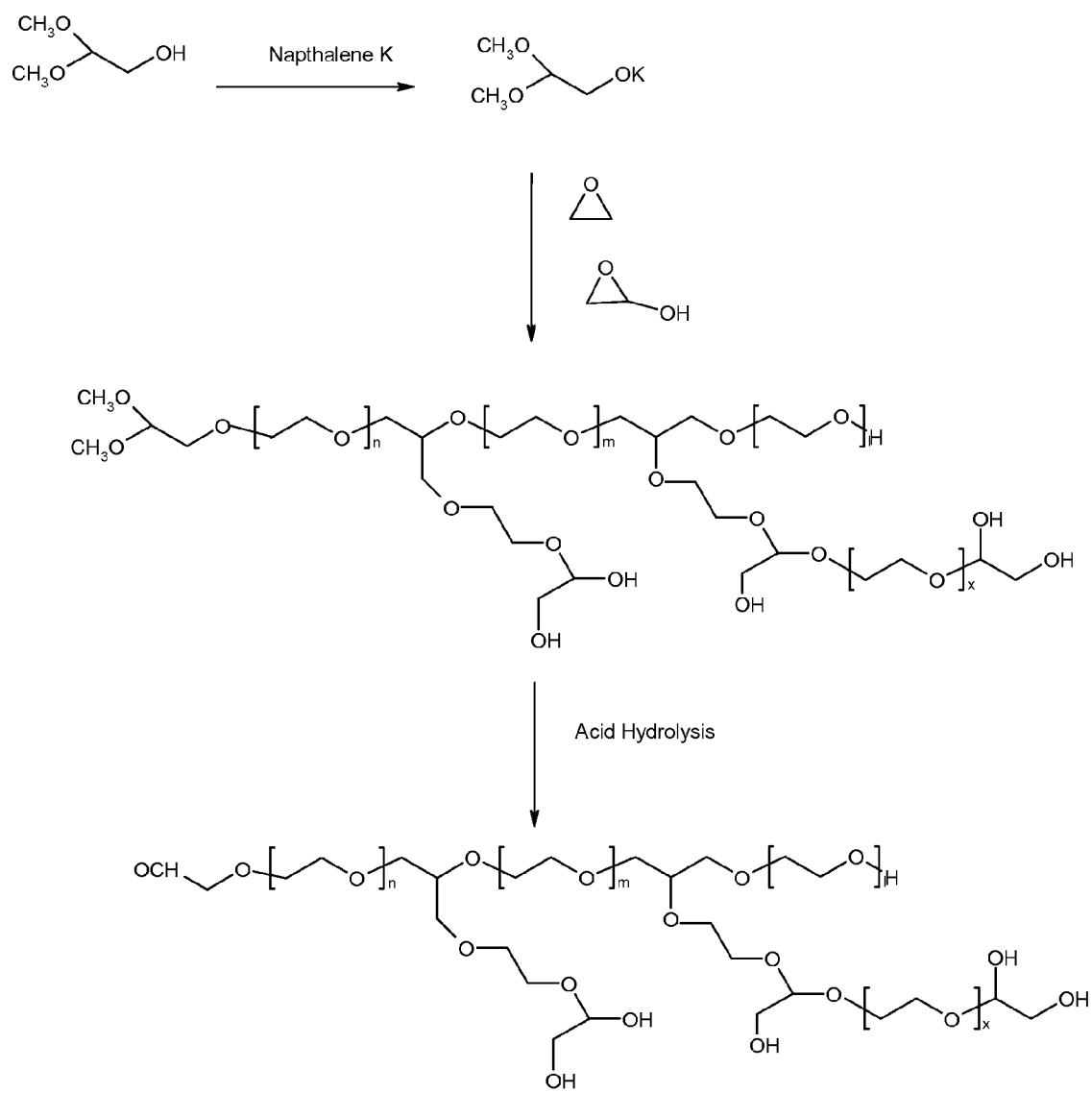

FIG. 3 discloses a schematic representation of a hyperbranched copolymer, which after deprotection, yields an aldehyde group at one end of the copolymer, and hydroxyl groups at the other termini's.

Figure 4:
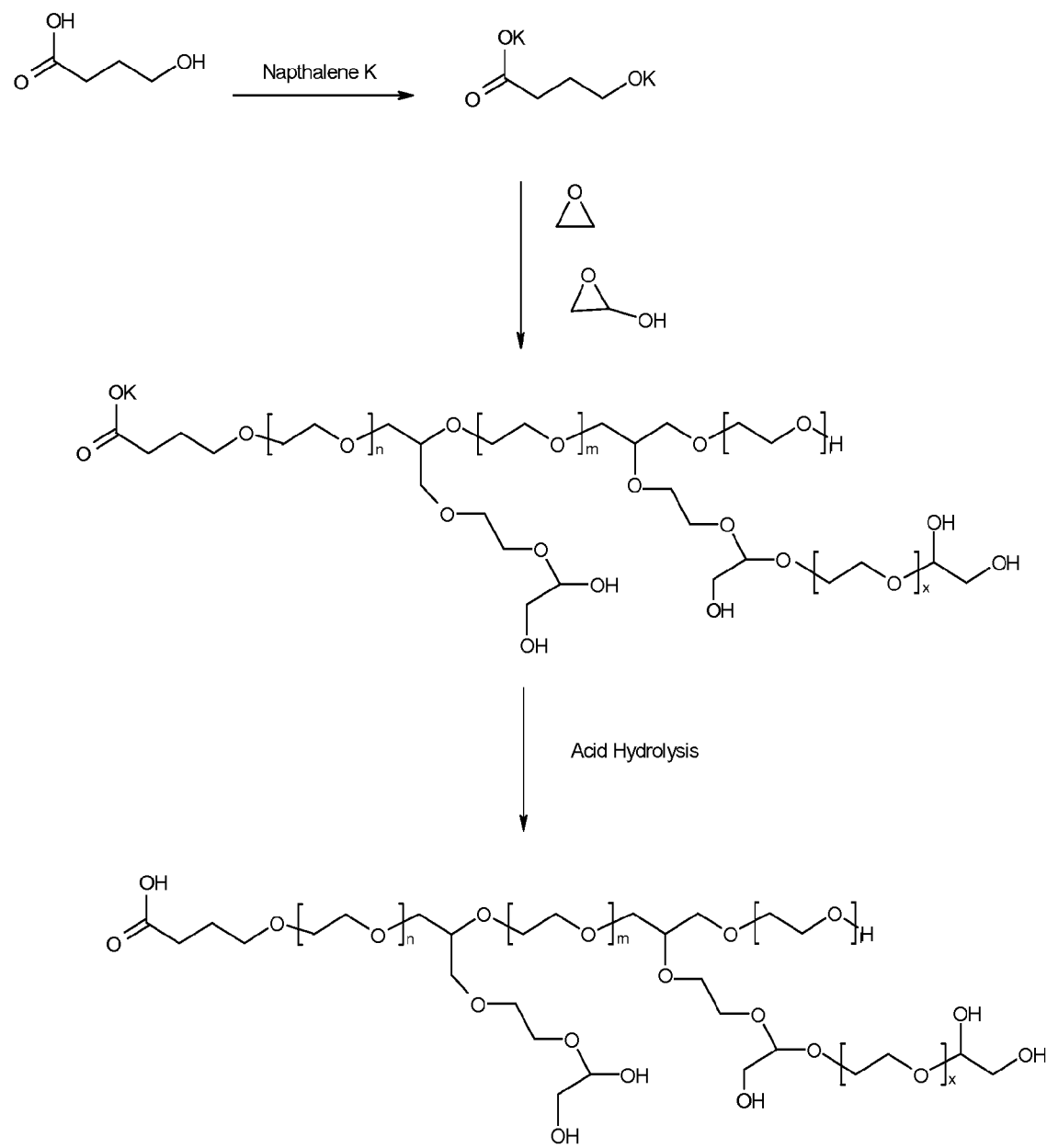

FIG. 4 discloses a schematic representation of a heterofunctional hyperbranched having a carboxyl functional group at one end and multiple hydroxy groups at the other termini's.

SUMMARY OF THE INVENTION

The heterofunctional copolymer of the present invention is a copolymer of glycerol and polyethylene glycol, wherein the copolymer has a random or block architecture. (See FIG. 1). The copolymers of the invention may be prepared from glycidol and ethylene oxide monomers.

The present invention also relates to conjugates of these copolymers with bioactive agents, and therapeutic polypeptides.

The present invention relates to conjugates of these copolymers to hydrophobic polymers, and the resultant amphiphilic copolymers are capable of forming polymeric micelles, which can be used as delivery systems for bioactive agents.

The present invention also relates to the conjugates of the copolymers with lipids, and such lipid-copolymer conjugates are capable of forming liposomes, which can act as delivery systems for bioactive agents. These liposomes exhibit long circulation half-lives.

DETAILED DESCRIPTION OF THE INVENTION

I. Heterofunctional Copolymers

A. Description of the Heterofunctional Copolymers

The heterofunctional copolymers of the present invention are a copolymer of glycerol and polyethylene glycol, wherein the copolymer has a random or block architecture. In one embodiment of the present invention the copolymers are prepared from glycidol and ethylene oxide monomers.

One aspect of the present invention are compounds represented by the structure:

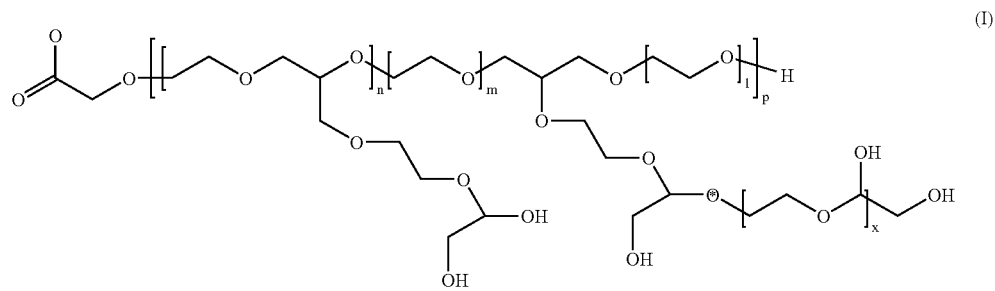

(I)

wherein
l is an integer having the value of 0 to 10,000;
m is an integer having the value of 0 to 10,000;
n is an integer having the value of 1 to 100;
p is an integer having the value of 1 to 100; and
x is an integer having the value of 1 to 100.

Another aspect of the present invention are compounds represented by the structure:

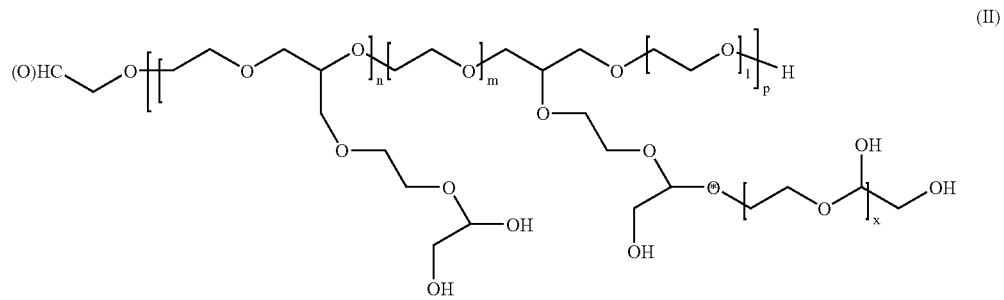

(II)

wherein
l is an integer having the value of 0 to 10,000;
m is an integer having the value of 0 to 10,000;
n is an integer having the value of 1 to 100;
p is an integer having the value of 1 to 100; and
x is an integer having the value of 1 to 100.

Another aspect of the present invention are compounds represented by the structure:

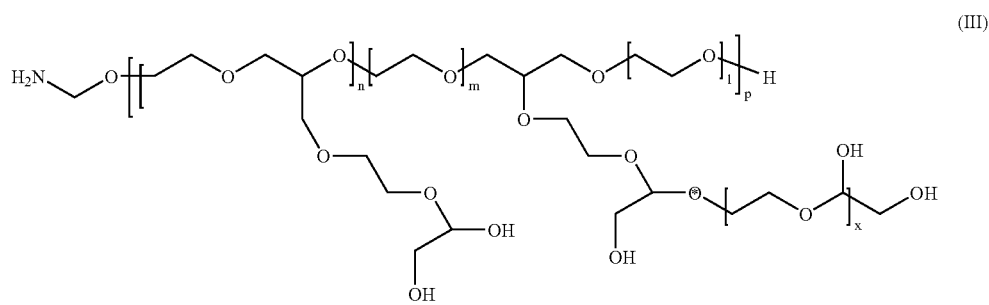

(III)

wherein
l is an integer having the value of 0 to 10,000;
m is an integer having the value of 0 to 10,000;
n is an integer having the value of 1 to 100;
p is an integer having the value of 1 to 100; and
x is an integer having the value of 1 to 100.

Another aspect of the present invention are compounds represented by the structure:

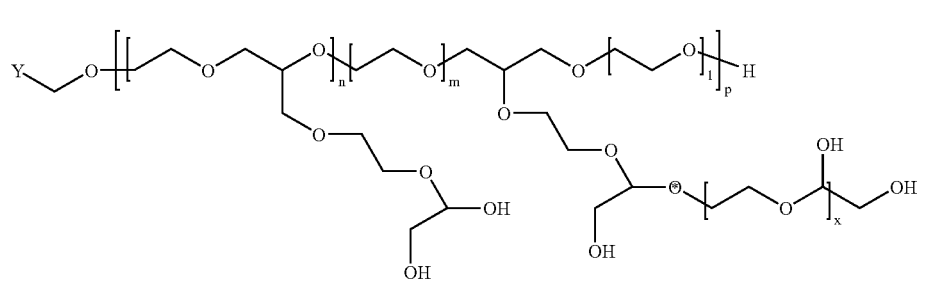

(IV)

wherein
Y is a an active agent, a hydrophobic polymer, or a lipid;
l is an integer having the value of 0 to 10,000;
m is an integer having the value of 0 to 10,000;
n is an integer having the value of 1 to 100;
p is an integer having the value of 1 to 100; and
x is an integer having the value of 1 to 100.

Another aspect of the present invention are compounds represented by the structure:

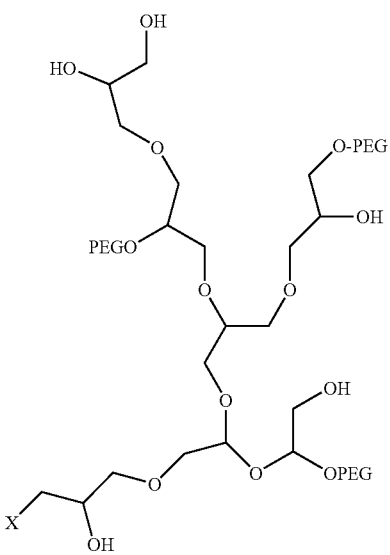

(V)

wherein

X is NH$_2$, CHO, COOH or modifications thereof; and

PEG is a repeating unit of polyethylene glycol having a molecular weight from about 500 to about 20,000 mw.

Another aspect of the present invention are compounds represented by the structure:

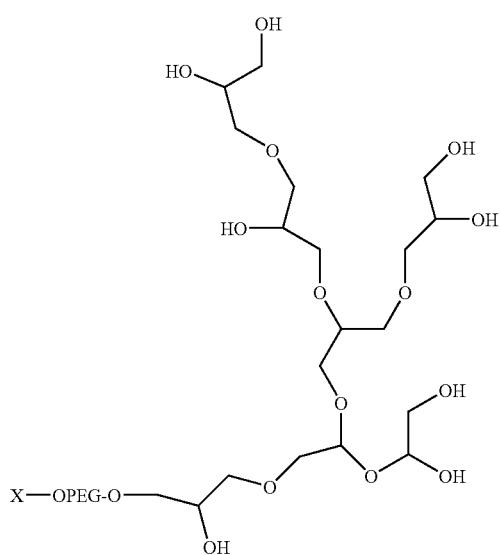

(VI)

wherein

X is NH$_2$, CHO, COOH or modifications thereof; and

PEG is a repeating unit of polyethylene glycol having a molecular weight from about 500 to about 20,000 mw.

According to the present invention, the active agent(s), hydrophobic polymers and lipids are chemically bound to the heterofunctional copolymer. Chemical conjugation of the heterofunctional copolymer to a water insoluble active agent, for instance, will effectively enhance the solubility of the active agent, and therefore improve its efficacy in the human body.

The chemical conjugation of the heterofunctional copolymer to a polypeptide, as an active agent, is meant to address and improve the delivery of protein therapeutics. During in vivo use, many proteins are cleared from circulation too rapidly. Some proteins have less water solubility than is optimal for a therapeutic agent that circulates through the bloodstream. Some proteins give rise to immunological problems when used as therapeutic agents. Immunological problems have been reported from manufactured proteins even where the compound apparently has the same basic structure as the homologous natural product.

For in vivo use, the polymer cloud can help to protect the compound from chemical attack, to limit adverse side effects of the compound when injected into the body, and to increase the size of the compound. Potentially this may render useful compounds that have some medicinal benefit, but otherwise are not useful, or even harmful to an organism. For example, the polymer cloud surrounding a protein can reduce the rate of renal excretion and immunological complications and can increase resistance of the protein to proteolytic breakdown into simpler, inactive substances.

Chemical conjugation of the heterofunctional copolymer to a hydrophobic, and biocompatible, polymer leads to the formation of amphiphilic block copolymers capable of spontaneously self assembling in water to form polymeric micelles. Such hydrophobic polymers include but are not limited to: polyesters, e.g., polylactic acid, polymalic acid, polycaprolactone, polydioxanone, polycarbonates, polyanhydrides, polyorthoesters; hydrophobic derivatives of poly (alpha-amino acids) such as described for hydrophilic polymers; polyalkyl ethers (e.g., polypropylene glycols); copolymers thereof; and derivatives of the foregoing.

In another aspect of the present invention, the chemical conjugation of the heterofunctional copolymer to lipid, suitably an amphiphilic lipid, leads to an amphiphilic lipid-copolymer conjugate, which is capable of forming, or can be incorporated into a liposome. These lipid-copolymer conjugates can thus be used as delivery systems or vehicles, for bioactive agents of choice. The liposomes are expected to exhibit longer circulation half-lives than administration of the agent alone.

B. Methods of Making the Heterofunctional Copolymers

The heterofunctional copolymer of the present invention is a copolymer of glycerol and polyethylene glycol, wherein the copolymer has a random or block architecture. (See FIG. 1). These copolymers of invention may be prepared from glycidol and ethylene oxide monomers.

It is known in the literature that controlled polymerization of glycidol can lead to hyperbranched polyglycerols. Presence of ethylene oxide in the reaction mixture produces copolymers of ethylene oxide and glycerol (Ph. Dimitrov, Polymer 43 (2002) 7171–7178). The architecture of the copolymer is dictated by the ratio of glycidol to ethylene oxide, as well as on the order of addition in which monomers are added to the polymerization medium, and their rate of addition to the mixture, which can also include continuous feed of the monomers. As a representative example of the above, a mixture of ethylene oxide and glycidol can lead to random copolymers of glycidol and ethylene oxide, see Example 1 in FIG. 1. Initiating polymerization of glycidol in the absence of ethylene oxide, can lead to a highly branched polyglycidol, which if further treated with ethylene oxide, produces block copolymer of polyglycidol and polyethylene glycol. These block copolymers contain branched polyglycidol, to which polyethylene oxide blocks are attached, see Example 2 in FIG. 1. However, if the ethylene oxide is polymerized first and glycidol is then added, the resultant block copolymer will have a different architecture, see as see in Example 3 in FIG. 1.

An important feature of this invention is the presence of the two different types of functional groups at the extremities of the hyperbranched copolymer of polyethylene oxide and polyglycidol. The presence of two different types of functional groups facilitates the selective use of one type functional group for the conjugation of one or more of therapeutic bioactive agents, hydrophobic polymers, and lipids.

For example, the "copolymer", may have a carboxylic group at one terminus and hydroxyl group at all other termini. In this embodiment, the carboxylic group may be used to conjugate to therapeutic bioactive agents, hydrophobic polymers, and lipids. It is well understood, that the carboxylic group may be activated or converted to any suitable reactive species for such conjugation.

In another embodiment, it is possible to have at least two different types of functional groups on the copolymer which may be an amino group at one terminus and hydroxyl groups at the other terminii's. Here, as the amino group is more reactive than the hydroxyl group, it can be reacted and used for the conjugation with the desired bioactive agent, hydrophobic polymer, and lipids. A third embodiment is the presence of an aldehyde group at one terminus and hydroxyl groups at the other terminii's with similar reaction and conjugation of the bioactive agents, hydrophobic polymers, and lipids.

As another aspect of the invention, it is also recognized that due to the ability to have these additional functional groups, such as the free hydroxyl groups scattered throughout the architecture, it is possible to also attach small molecules, as active agents onto these additional groups, thereby creating a higher load, or a more diverse load, of active agents to be delivered, irrespective of the functional group at one end of the terminus which is used to conjugate the initial bioactive agent, hydrophobic polymer, or lipid to the heterofunctional copolymer.

The synthesis of heterofunctional hyperbranched copolymer of polyethylene oxide and polyglycidol may be performed by applying methods described in the literature. Anionic polymerization is one method of choice for the synthesis of these copolymers.

For example U.S. Pat. No. 5,679,765 describes a process for the preparation of a polyether having a amine group at one terminus and a hydroxy group at the other, by using potassium bis(trimethylsilyl)amide as a polymerization initiator in polymerization of an epoxy compound, as well as an anionic polymerization initiator comprising potassium bis(trimethylsilyl)amide. When the anionic ring opening polymerization of ethylene oxide and glycidol is carried out by using alkali metal salt of bis(alkylsilyl)amide or of phthalimide as a polymerization initiator, the final copolymer will possess $(R_3Si)_2N$ group at one terminus and the other terminii will be hydroxy groups. This copolymer on reaction with a weak acid will be converted to primary amino group by removing the trimethylsilyl protecting group.

The amino group ($NH_2$) at one end originates in the polymerization initiator, so that the amino group is present in every polymer chain. This is also a characteristic feature of the polyethers as described herein. Another end of the polyether is the nucleophilic group —OK into which a wide variety of functional groups can be introduced by reaction of this terminal with a tosyl group, etc. In addition, bis(alkylsilyl)amide originating in the polymerization initiator, may be reacted with a suitable reagent and thereby converted into a functional group other than the primary amino group and different from another end, whereby a polyether having an arbitrary combination of different kinds of terminal functional groups can be synthesized.

FIG. 2 shows polymerization of ethylene oxide using potassium bis(trimethylsilyl)amide. The polymerization proceeds with a typical active anion species, so that there is no termination of polymerization, and a straight-chain polyethylene oxide of extremely narrow molecular weight distribution can be obtained. In addition, a polymer with an arbitrary molecular weight can be obtained by a change in a "monomer/polymerization initiator" ratio. That is, the average polymerization degree of the resulting polymer is almost the same as "number of moles of monomer/number of moles of polymerization initiator".

Application of this synthetic strategy to the copolymerization of ethylene oxide and glycidol, leads to the formation of a hyperbranched copolymer having amino group at one end, and hydroxyl groups at the other ends.

Other, different sets, of functional groups may be introduced at the extremities of the "copolymer", by using hydroxy aldehydes, wherein the aldehyde group may be protected and the anionic copolymerization of ethylene oxide and glycidol may be initiated through the alkali or alkaline earth metal salt of the hydroxy group. The resultant hyperbranched copolymer after deprotection yields an aldehyde group at one end and hydroxyl groups at the other ends (FIG. 3).

A third strategy to produce heterofunctional hyperbranched copolymers is described in US 2003/0027929, which does not involve protection of functional groups during anionic polymerization. Accordingly a metal ion salt of a hydroxycarboxylic acid is used as the initiator. The metal ion may be selected from Li, Na, K and Cs. Co-polymerization of ethylene oxide and glycidol are initiated at the hydroxyl group, leading to carboxyl functional group at one end and multiple hydroxy groups at the other termini (FIG. 4).

Copolymerization is carried out under an inert atmosphere and in a solvent. Once polymerization is completed, it is terminated by adding an acid, such as acetic acid, dichloroacetic acid and hydrochloric acid. The solvent is may be selected from tetrahydrofuran, dioxane, the N,N-dimethyl formamide, dimethylsulfoxide, ethylene glycol dimethylether and mixtures thereof.

The copolymerization may be carried out at about 50° C. in the presence of a suitable solvent.

C. Conjugation of the Copolymer to Liposome Components or Other Bioactive Molecules Chemical Conjugation Methods: In general the covalent attachment of the hetero functional copolymers to a bioactive molecule or a vesicle-forming lipid is accomplished by activation of chemical groups at one polymer end prior to reaction with a vesicle-forming lipid. A terminal amine or carboxyl group may be activated for coupling to the bioactive molecule or a lipid by monofunctional activating agents, such as N-hydroxysuccinimide, ethylchloroformate, DCCD, Woodward's Reagent K, cyanuric acid and trifluoromethanesulfonyl chloride among others. A number of bi-functional crosslinking reagents containing groups with different reactivities, such as some of the diisocyanates, may also be used to activate copolymers prior to coupling to lipid components.

Another embodiment of the present invention for activating copolymers for attachment to a phospholipid is illustrated in FIG. 4. In this reaction the terminal carboxyl group of the polymer is activated by reaction with N-hydroxysuccinimide. After this activation step the polymer is reacted with an amino group-containing phospholipid, such phosphatidylethanolamine, to generate the copolymer derivatized vesicle-forming lipid which is part of the composition of the invention.

An important feature of the amphiphilic lipid to be used in the lipid-copolymer conjugate is that the lipid contains a functional group at its polar head group suitable for covalent attachment to the heterofunctional copolymer chain. The polar head group is, for example, a primary or secondary amine group, a hydroxyl group, an aldehyde group, a halide or a carboxylic group. The hydrophobic moiety of the lipid enables the incorporation of the lipid-copolymer conjugates into bilayer structures, such as liposomes and acts as an anchor. The derivatized lipid components of liposomes according to the present invention may additionally include a labile lipid-polymer linkage, such as a peptide, ester, or disulfide linkage, which is known in the art, and which can be cleaved under selective physiological conditions, such as in the presence of peptidase or esterase enzymes or reducing agents. Use of such linkages to couple polymers to phospholipids allows the attainment of high blood levels of such liposomes for several hours after administration, followed by cleavage of the reversible linkages and removal of the polymer from the exterior liposome bilayer. The polymer-less liposomes are then subject to rapid uptake by the RES system, See, e.g., U.S. Pat. No. 5,356,633 to Woodle et al.

II. Preparation of the Liposome

A. Liposome Components

The amphiphilic lipids to be used in the lipid-copolymer conjugate may be a variety of synthetic or naturally occurring lipids, having at least one hydrophobic a polar tail and a hydrophilic polar head group, such as vesicle forming lipids and membrane lipids. There are a variety of synthetic vesicle-forming lipids and naturally-occurring vesicle-forming lipids, including those where the two hydrocarbon chains may be between about 14–22 carbon atoms in length, and having varying degrees of unsaturation. At least one of the novel copolymer conjugated lipids described above may also be included in the liposome of the invention.

Examples of suitable amphiphilic lipids include but are not limited to: phospholipids, glycolipids, ceramides, cholesterol and derivatives, saturated or partially unsaturated, branched or straight-chain $C_5$–$C_{80}$ mono- or dialkylamines, arylalkylamines, cycloalkylamines, alkanols, aldehydes, carbohalides or alkanoic acids and the anhydrides thereof.

Representative examples of these amphiphilic lipids are phosphatidyl choline, phosphatidyl ethanolamine, phosphatidyl inositol, phosphatidylglycerol, phosphatidic acid, phosphatidylserine, sphingomyelin, stearylamine, myristylalcohol, cholesterol and its derivatives; and palmitic acid.

An example of an amphiphilic heterofunctional copolymer-lipid conjugate is a lipid having two hydrophobic chains, typically alkyl chains, and a polar head group, containing a functional group, such as described above. Phosphatidyl ethanolamine derivatives and in particular distearyl phosphatidyl ethanolamine, are such phospholipids group, as they contain a reactive amino group. Another suitable amphiphilic lipid has as the hydrophilic polar head group a primary or secondary amine and two saturated or unsaturated $C_5$–$C_{80}$ branched or straight chain hydrophobic apolar moieties. Examples thereof are, 1-heptadecyloctadecylamine and distearylamine-containing compounds, such as distearylamine and N-succinyl dioctadecylamine (also referred to herein as DODASuc).

Representative liposomes for use herein comprise:
HSPC (about 10 to about 90 mol %) Cholesterol (0 to about 60 mol %, or 30 to 50 mol %) copolymer-DSPE conjugate (0–20 mol %, or 0 to about 5 mol %); or
DSPC (about 10 to about 90 mol %) Cholesterol (0 to about 60 mol %, or about 30 to 50 mol %) copolymer-DSPE conjugate (0 to about 20 mol %, also 0 to about 5 mol %); or
POPC (about 10 to about 90 mol %) Cholesterol (0 to about 60 mol %, or about 30 to about 50 mol %) copolymer-DSPE conjugate (0 to about 20 mol %, also 0 to about 5 mol %); or
Sphingomyelin (about 10 to about 90 mol %) Cholesterol (0 to about 60 mol %, or about 30 to about 50 mol %) copolymer-DSPE conjugate (0 to about 20 mol %, also 0 to about 5 mol %); or
POPC (about 80 to about 99.5 mol %) copolymer-DSPE conjugate (0 to about 20 mol %, or 0 to about 5 mol %); or
DSPC (about 10 to about 90 mol %) Cholesterol (0 to about 60 mol %, or about 30 to about 50 mol %) copolymer-Cholesterol conjugate (0 to about 20 mol %, or 0 to about 5 mol %).

The liposome membrane can also contain preservatives, such as, for example, tocopherol as an antioxidant. The liposome may also contain conjugates of sugars and hydrophobic components, such as, for example, palmitic or stearic acid esters of dextran.

In another embodiment, the liposome components are selected to achieve a specified degree of fluidity or rigidity, to control the stability of the liposome in serum and/or to control the rate of release of the entrapped agent in the liposome. Liposomes having a more rigid lipid bilayer, or a liquid crystalline bilayer, may be achieved by incorporation of a relatively rigid lipid, e.g., a lipid having a relatively high phase transition temperature, e.g., above room temperature, such as, for example, above body temperature and up to 80° C. Rigid, i.e., saturated, lipids contribute to greater membrane rigidity in the lipid bilayer. Other lipid components, such as cholesterol, are also known to contribute to membrane rigidity and stability in lipid bilayer structures.

On the other hand, lipid fluidity may be achieved by incorporation of a relatively fluid lipid, typically one having a lipid phase with a relatively low liquid to liquid-crystalline phase transition temperature, e.g., at or below room temperature.

Vesicle-forming lipids having a main phase transition temperatures from approximately 2° C.–80° C. may be used as a primary liposome component of the present composition. In one embodiment of the invention, a vesicle-forming lipid having a main phase transition temperature above about 37° C. is used as the primary lipid component of the liposomes. In another embodiment, a lipid having a phase transition temperature between about 37–70° C. is used. By way of example, the lipid distearoyl phosphatidylcholine (DSPC) has a main phase transition temperature of 55.1° C. and the lipid hydrogenated soy phosphatidylcholine (HSPC) has a phase transition temperature of 58° C. Phase transition temperatures of many lipids are tabulated in a variety of sources, such as Avanti Polar Lipids catalogue and Lipid Thermotropic Phase Transition Database (LIPIDAT, NIST Standard Reference Database 34).

Thermal or pH release characteristics can optionally be built into liposomes by incorporating thermal sensitive or pH sensitive lipids as a component of the lipid bilayer (e.g., dipalmitoyl-phosphatidylcholine:distearyl phosphatidylcholine (DPPC:DSPC) based mixtures. Use of thermal or pH sensitive lipids allows controlled degradation of the lipid vesicle membrane.

The liposome components discussed are available commercially or may be prepared using methods known in the art.

B. Preparation of the Liposomes from Liposome Components

Preparation of liposomes is well known in the art and such known methods may be used in the present invention. In general, liposome formation involves preparing a mixture of vesicle-forming lipids in powder form, dissolving the mixture in an organic solvent, freeze-drying the solution (lyophilising), removing traces of solvent, reconstituting the mixture with buffer to form multilamellar vesicles, and optionally extruding the solution through a filter to form large or small unilamellar vesicles. The pH, temperature and total lipid ratio are selected according to principles well known in the art so as to form the lipid bilayers. Examples of methods of forming liposomes suitable for use in the invention include those described by L. D. Mayer et al., Vesicles of Variable Sizes Produced by a Rapid Extrusion Procedure, B.B.A. 858(I); 161–8, 1986; Szoka, F., Jr. et al., Ann. Rev. Biophys. Bioeng. 9:467 (1980); and U.S. Pat. Nos. 5,077,056; 5,013,556; 5,631,018 and 5,395,619.

For ease of manufacture, the copolymer-lipid conjugate is may be incorporated into the liposomes during their preparation, i.e., the conjugate is present during formation of the bilayer. In this embodiment, the conjugate is included in the mixture of powdered lipid materials used to prepare the liposomes such as described above. The resulting liposomes tend to have the receptor antagonist present on both the inner and the outer surface of the lipid bilayer.

Alternatively, the copolymer-lipid conjugate can be incorporated into the liposomes after their formation, i.e., the copolymer-lipid conjugate is inserted in the bilayer after formation of the bilayer. In this embodiment the copolymer tends to be present only on the external surface of the lipid bilayer. In this embodiment, the copolymer-lipid conjugate is dissolved in a suitable solvent and the resulting solution is incubated with the liposomes under gentle mixing (e.g., stiffing) for a time effective for the copolymer-lipid conjugate to assemble in the liposomes' lipid bilayer.

In another exemplary formulation procedure, a therapeutic active agent, such as a drug or other compound, for inclusion into the liposome is first dispersed by sonication in a surfactant (optionally including copolymer-grafted lipids) that readily solubilizes hydrophobic molecules. The resulting micellar suspension of the drug or compound is then used to rehydrate a dried lipid sample that contains a suitable mole percent of copolymer-grafted lipid, or cholesterol. The suspension is then formed into liposomes using extrusion techniques as are known in the art, and the resulting liposomes, optionally, separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See, e.g., U.S. Pat. No. 4,737,323.

After liposome formation, the vesicles may be sized to achieve a size distribution of liposomes within a selected range, such as from 0.03 to 0.5 μm, according to known methods. Small unilamellar vesicles (SUVs), typically in the 0.04 to 0.08 μm range, can be prepared by extensive sonication or homogenization of the liposomes. Homogeneously sized liposomes having sizes in a selected range between about 0.08 to 0.4 μm can be produced, e.g., by extrusion through polycarbonate membranes or other defined pore size membranes having selected uniform pore sizes ranging from 0.03 to 0.5 μm, such as for example, 0.05, 0.08, 0.1, or 0.2 μm. The pore size of the membrane corresponds roughly to the largest size of liposomes produced by extrusion through that membrane, particularly where the preparation is extruded two or more times through the same membrane. The sizing may be carried out in the original lipid-hydrating buffer, so that the liposome interior spaces retain this medium throughout the initial liposome processing steps.

The liposome suspensions that are obtained according to this invention may be stored directly or after adjuvants are added or first further processed (e.g., freeze-drying or spray-drying).

C. Definitions

In order for the present invention to be more readily understood, certain terms are defined herein. Additional definitions are set forth throughout the detailed description.

The term "antibody," as used herein, refers to an immunoglobulin or a fragment or derivative thereof, and encompasses any polypeptide comprising an antigen-binding site regardless of the source, method of production (in vitro or in vivo), and other characteristics. The term includes but is not limited to polyclonal, monoclonal, monospecific, polyspecific, non-specific, humanized, single-chain, chimeric, synthetic, recombinant, hybrid, mutated, and CDR-grafted antibodies. Unless otherwise modified by the term "intact," as in "intact antibodies," for the purposes of this disclosure, the term "antibody" also includes antibody fragments such as Fab, $F(ab')_2$, Fv, scFv, Fd, dAb, and other antibody fragments that retain antigen-binding function, i.e., the ability to bind an antigen specifically. Typically, such fragments would comprise an antigen-binding domain. The term "antigen-binding domain" refers to the part of an antibody molecule that comprises the area specifically binding to or complementary to a part or all of an antigen.

A "copolymer" is a polymer that is formed by linking at least two types of small molecules (or monomers) together, as compared to a homopolymer, which is formed by linking only one type of small molecule (or monomer) together. The copolymers may be employed as alternating, random, block, graft, or hyperbranched copolymers. In an alternating copolymer, the monomers are arranged in an alternating fashion. In a random copolymer, the different monomer units are arranged randomly. In a block copolymer, the monomer units are arranged by grouping all of the first type together and linking them to a group of all of the second type of monomers together. In a graft copolymer, chains of one monomer are grafted onto a polymer chain of the other monomer. In a hyperbranched copolymer, chains of the monomers are arranged in a branched fashion, as compared to an exclusively linear fashion. Hyperbranched copolymers may be further described as random hyperbranched copolymers, alternating hyperbranched copolymers, etc.

"Liposome" means an artificial vesicle that is composed of one or more phospholipid-containing bilayers.

"Polymeric Micelle" is a self assembled structure formed from an amphiphilic copolymer, composed of hydrophobic and hydrophilic polymer segments. During the self assembly of the amphphilic copolymer in aqeous media, a core shell structure of polymeric micelle is fromed. The inner core is composed of hydrophobic polymer whereas the outer shell is derived from the hydrophilic polymer.

"Phospholipid" means a phosphorous-containing lipid with a hydrophobic tail composed of two fatty acid chains and a hydrophilic polar head groups that contains the phosphate.

The term "nucleic acid" refers to deoxyribonucleic acid (DNA), ribonucleic acid (RNA), or peptide nucleic acid (PNA, an analog of DNA in which the phosphate background is replaced with an uncharged peptide-like backbone). The term should also be understood to include nucleotide analogs, and single or double stranded polynucleotides (e.g., siRNA). Examples of polynucleotides include but are not limited to plasmid DNA or fragments thereof, viral DNA or RNA, antisense RNA, etc. The term "plasmid DNA" refers to double stranded DNA that is circular. "Antisense," as used herein, refers to a nucleic acid capable of hybridizing to a portion of a coding and/or noncoding region of mRNA by virtue of sequence complementarity, thereby interfering with translation from the mRNA. The terms "siRNA" and "RNAi" refer to a nucleic acid which is a double stranded RNA that has the ability to induce degradation of mRNA thereby "silencing" gene expression. Typically, siRNA is at least 15–50 nucleotides long, e.g., 20, 21, 22, 23, 24, 25, 26, 27, 28, 29, or 30 nucleotides in length.

"Targeting moiety" refers to a moiety that assists in the delivery of the liposome to a particular portion of the body, a particular cell or tissue type, or a particular diseased region. Targeting moieties that bind to a diseased tissue, particular cell type, tissue type, or that are directed to a particular portion of the body may be used to assist in localization of the liposome to the desired area for treatment or diagnosis purposes. Targeting moieties include, but are not limited to, antibodies; chemical agents; cytokines; enzymes; haptens; hormones; non-protein molecules which confer a particular enzymatic or surface recognition feature to the liposome; peptides; proteins; and small molecules.

"Therapeutic active agent" includes, but is not limited to, drugs, proteins, peptides, nucleic acids, nutritional agents, as described herein. This term includes pharmaceutically acceptable agents, bioactive agents, active agents, therapeutic agents, therapeutic proteins, diagnostic agents, or drug(s) as defined herein, and follows the guidelines from the European Union Guide to Good Manufacturing Practice. Such substances are intended to furnish pharmacological activity or other direct effect in the diagnosis, cure, mitigation, treatment, or prevention of disease or to affect the structure and function of the body. The substance may also include a diagnostic agent, such as an imaging agent and/or a radioactive labelled compound. Their use may be in a mammal, or may be in a human. The pharmacological activity may be prophylactic, or for treatment of a disease state. The agents herein include both small molecule therapeutics, as well as peptides and proteins. The pharmaceutical compositions described herein may optionally comprise one or more pharmaceutically acceptable active agent, bioactive agent, active agent, therapeutic agent, therapeutic protein, diagnostic agent, or drug(s) or ingredients distributed within.

"Vesicle-forming lipid" as used herein generally means any amphipathic lipid having hydrophobic and head group moieties (either polar or nonpolar), and which can form spontaneously into bilayer vesicles in water (as exemplified by phospholipids), or lipids which are stably incorporated into lipid bilayers in combination with other lipids such as phospholipids. When formed into vesicles, the hydrophobic moiety of a vesicle-forming lipid is in contact with the interior hydrophobic region of the bilayer membrane, and the head group moiety is oriented toward the surface of the membrane.

D. Loading of Compounds into Interior of Liposome

1. Compounds for Loading into the Interior of the Liposome

In another embodiment of the present invention the liposomes comprise a therapeutic or diagnostic agent which is entrapped in the liposome, for delivery to a desired disease site. Of course, selection of a particular agent will be made depending on the disease being treated, or diagnosed. Selection of the therapeutic or diagnostic agent will be made based on the nature of the disease site and the activity of the agent toward that site, which may be determined, for example, on chemosensitivity testing according to methods known in the art, or on historical information, and/or on accepted clinical practice.

The agent(s) can be either conjugated to the heterofunctional copolymer of the present invention, or incorporated into the colloidal carrier compositions, derived from the heterofunctional copolymer, in an amount sufficient to obtain the desired effect.

Therapeutic agents may be selected, for example, from natural or synthetic compounds having the following activities: anti-angiogenic, anti-arthritic, antiarrhythmic, anti-bacterial, anti-cholinergic, anti-coagulant, anti-diuretic, antiepilectic, anti-fungal, anti-inflammatory, anti-metabolic, anti-migraine, anti-neoplastic, anti-parasitic, anti-pyretic, anti-seizure, anti-sera, anti-spasmodic, analgesic, anaesthetic, beta-blocking, biological response modifying, bone metabolism regulating, cardiovascular, diuretic, enzymatic, fertility enhancing, growth-promoting, hemostatic, hormonal, hormonal suppressing, hypercalcemic alleviating, hypocalcemic alleviating, hypoglycaemic alleviating, hyperglycaemic alleviating, immunosuppressive, immunoenhancing, muscle relaxing, neurotransmitting, parasympathomimetic, sympathominetic plasma extending, plasma expanding, psychotropic, thrombolytic and vasodilating. Cytotoxic therapeutic agents are a class of agent, which has been extensively utilized in liposomal inventions.

Representative examples of these therapeutic agents that can be delivered in this invention include but are not limited to: topoisomerase I inhibitors, topoisomerase III inhibitors, anthracyclines, vinca alkaloids, platinum compounds, antimicrobial agents, quinazoline antifolates thymidylate synthase inhibitors, growth factor receptor inhibitors, methionine aminopeptidase-2 inhibitors, angiogenesis inhibitors, coagulants, cell surface lytic agents, therapeutic genes, plasmids comprising therapeutic genes, Cox inhibitors, RNA-polymerase inhibitors, cyclooxygenase inhibitors, steroids, and NSAIDs (nonsteroidal antiinflammatory agents).

Examples of Therapeutic Agents Include:

Topoisomerase I-inhibiting camptothecins and their analogs or derivatives, such as SN-38 ((+)-(4S)-4,1 1-diethyl-4,9-dihydroxy-IH-pyrano[3',4':6,7]-indolizine[1,2-b]quinoline-3,14(4H,12H)-dione); 9-aminocamptothecin; topotecan (hycamptin; 9-dimethyl-aminomethyl-10-hydroxycamptothecin); irinotecan (CPT-11; 7-ethyl-10-[4-(I-piperidino)-I-piperidino]-carbonyloxy-camptothecin), which is hydrolyzed in vivo to SN-38); 7-ethylcamptothecin and its derivatives (Sawada, S. et al., Chem. Pharm. Bull., 41(2): 310–313 (1993)); 7-chloromethyl-10,11 methylene-dioxy-carnptothecin; and others (SN-22, Kunimoto, T. et al., J. Pharmacobiodyn., 10(3):148–151 (1987); N-formylaniino-12,13,dihydro-I,I 1 25 dihydroxy-13-(beta-D-glucopyran-syl)-5H-indolo[2,3-a]pyrrolo[3,4-c]carbazole-5,7(6H)-dione (NB-506, Kanzawa, G. et al., Cancer Res., 55(13): 2806–2813 (1995); DX-895lf and lurtotecan (GW-211 or 7-(4-methylpiperazino-methylene)-10,11ethylenedioxy-20 (S)-carnptothecin) (Rothenberg, M. L., Ann. Oncol., 8(9): 837–855 (1997)); and 7-(2-(N-isopropylamino)ethyl)-(20S)-camptothecin (CKD602, Chong Kun Dang Corporation, Seoul Korea).

Topoisomerase I/II-inhibiting compounds such as 6-[[2-dimethylamino)ethyl]amino]-3-hydroxy-7H-indeno[2,1-c] quinolin-7-one dihydrochloride, (TAS 103, Utsugi, T., et al., Jpn. J. Cancer Res., 88(10):992–1002 (1997)); 3-methoxy-1 1H-pyrido[3'.4-4,5]pyrrolo[3,2-c]quinoline-1,4-dione (Aza-lQD, Riou, J. F., et al., Mol. Pharmacol., 40(5):699–706 (1991)).

Anthracyclines such as doxorubicin, daunorubicin, epirabicin, pirarubicin, and idarubicin; Vinca alkaloids such as vinblastine, vincristine, vinleurosine, vinrodisine, vinorelbine, and vindesine.

Platinum compounds, such as cisplatin, carboplatin, ormaplatin, oxaliplatin, zeniplatin, enloplatin, lobaplatin, spiroplatin, ((−)-(R)-2-aminomethylpyrrolidine (1,1-cyclobutane dicarboxylato)platinum), (SP-4-3(R)-1,1-cyclobutane dicarboxylato(2-)-(2-methyl-1,4-butanediamine-N,N)platinum), nedaplatin, and (bis-acetato-ammine-dichloro-cyclohexylamine-platinum(IV)).

Antimicrobial agents such as gentamicin and nystatin; Quinazoline antifolates thymidylate synthase inhibitors such as described by Hennequin et al. Quinazoline Antifolates Thymidylate Synthase Inhibitors: Lipophilic Analogues with Modification to the C2-Methyl Substituent (1996) J. Med. Chem. 39,695–704; Growth factor receptor inhibitors such as described by: Sun L. et al., Identification of Substituted 3-[(4.5,6,7-Tetrahydro-IH-indol-2-yl)methylene]-1,3-dihydroindol-2-ones as Growth Factor Receptor Inhibitors for VEGF-R2 (Flk I/KDR), FGF-RI, and PDGF-Rbeta Tyrosine Kinases (2000) J. Med. Chem. 43:2655–2663; and Bridges A J. et al. Tyrosine Kinase Inhibitors. An Unusually Steep Structure-Activity Relationship for Analogues of 4-(3-Bromoanilino)-6,7dimethoxyquinazoline (PD 153035): a Potent Inhibitor of the Epidermal Growth Factor Receptor (1996) J. Med. Chem. 39:267–276, Inhibitors of angiogenesis, such as angiostatin, endostatin, echistatin, thrombospondin, plasmids containing genes which express anti-angiogenic proteins, and methionine aminopeptidase-2 inhibitors such as fumagillin, TNP-140 and derivatives thereof, and other therapeutic compounds such as 5-fluorouracil (5-FU), mitoxanthrone, cyclophosphamide, mitomycin, streptozoein, mechlorethamine hydrochloride, melphalan, cyclophosphamide, triethylenethiophosphoramide, carmustine, lomustine, semustine, hydroxyurea, thioguanine, decarbazine, procarbazine, mitoxantrone, steroids, cytosine arabinoside, methotrexate, aminopterin, motomycin C, demecolcine, etopside, mithramycin, Russell's Viper Venom, activated Factor IX, activated Factor X, thrombin, phospholipase C, cobra venom factor [CVF], and cyclophosphamide.

Imaging agents include compounds in their gaseous state, such as oxygen, and radioactively labelled excipients, such as 3H-cholesteryloleylether.

In another embodiment, the therapeutic agent may be selected from: antineoplastic agents, such as topotecan, doxorubicin, daunorubicin, vincristine, mitoxantrone, carboplatin, RNA polymerase inhibitors, and combinations thereof; anti-inflammatory agents, such as cyclooxygenase inhibitors, steroids, and NSAIDs; anti-angiogenesis agents such as famagillin, tnp-140, cyclooxygenase inhibitors, angiostatin, endostatin, and echistatin; anti-infectives; and mixtures, or combinations thereof.

In another embodiment, the therapeutic active may be selected from topotecan, doxorubicin, daunorubicin, vincristine, mitoxantrone, RNA-polymerase inhibitors, and mixtures or combinations thereof. In certain embodiments, the therapeutic active agent is topotecan. Other camptothecins, and camptothecin analogs, are also useful therapeutic actives.

Nucleic acids may be incorporated into the liposome of the invention, such as deoxyribonucleic acid (DNA), ribonucleic acid (RNA), peptide nucleic acid (PNA), oligonucleotides, nucleotide analogs, single or double stranded polynucleotides, plasmid DNA or fragments thereof, viral DNA, antisense RNA and, siRNA or RNAi (referring to a nucleic acid which is a double stranded RNA that has the ability to induce degradation of mRNA thereby "silencing" gene expression and typically is at least 15–50 nucleotides long, e.g., 20, 21, 22, 23, 24, 25, 26, 27, 28, 29, or 30 nucleotides in length).

Nutritional agents suitable for incorporation into liposomes of the present invention include amino acids, sugars, proteins, carbohydrates, water soluble or fat soluble vitamins (such as vitamin C and vitamin E), or fat. Combinations of nutritional agents are also suitable.

Examples of diagnostic agents include contrast agents for imaging including paramagnetic, radioactive or fluorogenic ions. Specific imaging agents further include radiocontrast agents (such as radioisotopes like Tc or In, or compounds containing radioisotopes including iodo-octanes, halocarbons, and renografin), X-ray imaging agents (such as barium or lead), optical imaging agents (such as chromophores), magnetic resonance imaging agents (such as paramagnetic ions or paramagnetic compounds), and ultrasound contrast agents. Specific examples of such diagnostic agents include those disclosed in U.S. Pat. No. 5,855,866 issued to Thorpe et al. on Jan. 5, 1999.

2. Loading of Compounds into Liposome Interior or Conjugation of the Compounds to the Liposome Methods of incorporating therapeutic and diagnostic agents into liposomes are well known in the art and are useful in the present invention. Suitable methods include passive entrapment by hydrating a lipid film with an aqueous solution of a water-soluble agent or by hydrating a lipid film containing a lipophilic agent, pH ion gradient loading/retention (often called remote loading and employing gradients such as ammonium sulfate gradients), polymer gradient loading/retention, and reverse phase evaporation liposome preparation. For example, useful methods of loading such agents are described in Haran, G. et al., Transmembrane Ammonium Sulfate Gradients in Liposomes Produce Efficient and Stable Entrapment of Amphipathic Weak Bases, Biochim Biophys Acta, Vol 15 1, pp 201–215 (1993); U.S. Pat. No. 5,077,056 issued to Bally et al. on Dec. 31, 1991; 30 PCT Publication No. WO 98/17256, published Apr. 30, 1998; Zhu, et al., The Effect of Vincristine-Polyanion Complexes IN STEALTH Liposomes on Pharmacokinetics, Toxicity and Anti-Tumor Activity, Cancer Chemother. Pharmacol (1996) 39:138–142; and PCT Publication No. WO 00/23052. The agents can be incorporated into one or more of the liposomal compartments, or be bound to the liposome membrane.

Incorporation of the active agent by conjugation, such as on the terminus end of an amphiphilic polymer may be found in Zalipsky et al., Advanced Drug Delivery Reviews, 1995, 16, 157–182 and in Eur. Polym, J. 19(12), 1177–1183 (1983). See also Zhang, Yuan-Peng; Ceh, Boris; Lasic, Danilo D. Liposomes in drug delivery, Polymeric Biomaterials (2nd Edition) (2002), 783–821; Berg, Hermann. Medical applications of liposomes, D. Lasic, D. Papahadjopoulos, Bioelectrochemistry and Bioenergetics (1999), 48(2), 490; Lasic, Dan D. Novel applications of liposomes, Trends in Biotechnology (1998), 16(7), 307–321; and Lasic, Danilo G. Liposomes in drug delivery, Surfactant Science Series (1996), 62(Vesicles), 447–476.

a. Loading Procedures

Methods of incorporating therapeutic and diagnostic agents into liposomes are well known in the art and are useful in the present invention. Suitable methods include passive entrapment by hydrating a lipid film with an aqueous solution of a water-soluble agent or by hydrating a lipid film containing a lipophilic agent, pH ion gradient loading/retention (e.g., ammonium sulfate gradients), polymer gradient loading/retention, and reverse phase evaporation liposome preparation. For example, useful methods of loading such agents are described in Haran, G. et al., Transmembrane Ammonium Sulfate Gradients in Liposomes Produce Efficient and Stable Entrapment of Amphipathic Weak Bases, Biochim Biophys Acta, Vol 15 1, pp 201–215 (1993); U.S. Pat. No. 5,077,056 issued to Bally et al. on Dec. 31, 1991; 30 PCT Publication No. WO 98/17256, published Apr. 30, 1998; Zhu, et al., The Effect of Vincristine-Polyanion Complexes IN STEALTH Liposomes on Pharmacokinetics, Toxicity and Anti-Tumor Activity, Cancer Chemother. Pharmacol (1996) 39:138–142; and PCT Publication No. WO 00/23052. The agents can be incorporated into one or more of the liposomal compartments, or be bound to the liposome membrane.

E. Incorporation of Targeting Moiety in to the Liposome

1. Description of the Targeting Moiety

Optionally, the liposome may include a targeting moiety to assist in its delivery to a particular portion of the body, a particular cell or tissue type, or a particular diseased region. Targeting moieties that bind to a diseased tissue, particular cell type, tissue type, or that are directed to a particular portion of the body may be used to assist in localization of the liposome to the desired area for treatment, diagnosis, or imaging purposes. Targeting moieties include, but are not limited to, antibodies; chemical agents; cytokines; enzymes; haptens; hormones; non-protein molecules which confer a particular enzymatic or surface recognition feature to the liposome; peptides; proteins; and small molecules.

Such targeting moieties include antibodies that are known to bind to cancer antigens, such as those on tumor or cancerous cells, or on the tumor vascular epithelium. These include antibodies that bind against HER2 (such as described in PCT WO 99/55367), and the $\alpha_v\beta_3$ integrins.

2. Conjugation of the Targeting Moiety to the Phospholipid and Incorporation into the Liposome The targeting moiety may be attached to a liposome surface by covalent or noncovalent means. To attach a targeting moiety to a liposome surface covalently, a derivatized lipid containing an end-functionalized polyethylene glycol chain may be incorporated into the liposome. After liposome formation, the end-functionalized group can react with a targeting moiety for coupling to the liposome surface.

Alternatively, the targeting moiety may be first combined with a lipid to form a targeting moiety-lipid derivative and then incorporated into the liposome. For example, a targeting moiety may be coupled to a malemide group of a DSPE-copolymer molecule. The resulting targeting moiety-DSPE-copolymer conjugate may be used to form liposomes or may be combined with pre-formed liposomes.

If the targeting moiety is an antibody, such as an scFv antibody fragment, it may be expressed in a suitable recombinant system, such as *E. coli* cells. The expressed construct may have an engineered C-terminal sequence: GGGC. This C-terminal sequence provides a thiol group for convenient conjugation to the liposome. The recombinant expression cells are lysed and the scFv is isolated using protein A affinity chromatography, terminal cysteine reduction, and ion exchange chromatography.

The purified scFv antibody fragments are then conjugated to maleimido-copolymer-DSPE linker molecule in an aqueous solution at pH 6.2 and linker/protein molar ratio of approximately 4. The resulting conjugate is purified by size exclusion chromatography. The purified conjugate (in micellar form) is incubated with preformed, drug-loaded liposomes at the ratio of approximately 1 scFv for 1,300–2,600 liposome phospholipids, typically for 1 hour at 55–65° C.

In another method of the invention, targeting moieties can be coupled without requiring special reactive groups for coupling. Spacer arms or linkers can be tailored to achieve optimal coupling ratios and constructions of targeting moieties into the liposome. These techniques are well recognized in the art. (See, e.g., U.S. Pat. No. 4,762,915).

III. Methods of Using the Liposome

Liposomes of the present invention may be used for a variety of purposes, including, but not limited to, diagnosis of a disease or condition, imaging, and treatment of a disease or condition. For example, drugs or other active agents can be incorporated into the liposome as described, and administered to a patient. Encapsulated drugs may be protected by the liposome and, in certain instances, may be administered at lower dosages than unencapsulated drugs. In another embodiment, imaging agents can be incorporated into the liposome, then administered to a patient. These imaging agents can be used for various types of imaging, as discussed above. Imaging agents can be used to diagnose a disease or condition. In one embodiment, an imaging agent is encapsulated into a liposome coated with a targeting moiety. The targeting moiety may be, for example, an antibody to a cancer antigen. Such a liposome may be used to image and detect a particular form of cancer. Methods of using liposomes are well recognized and fully discussed in the art.

IV. Pharmaceutical Dosage Forms

In order to use the liposomes of the invention, they will normally be formulated into a pharmaceutical composition, in accordance with standard pharmaceutical practice. This invention therefore, also relates to a pharmaceutical composition, comprising an effective, non-toxic amount of the liposomes herein described and a pharmaceutically acceptable carrier or diluent. In another embodiment, the liposome will also incorporate the therapeutic active agent and a pharmaceutically acceptable carrier or diluent.

The liposomes of the invention and pharmaceutical compositions incorporating such may conveniently be administered by any of the routes conventionally used for drug administration, for instance, parenteral, oral, topical, by inhalation (e.g., intertracheal), subcutaneous, intramuscular, interlesional (e.g., to tumors), intranasal, intraocular, and by direct injection into organs and intravenous. In certain embodiments, parenteral administration, such as, for example intravenous administration may be used to administer the liposomes of the invention, and pharmaceutical compositions incorporating such. Where the liposomes are designed, for instance, intended to provide an anti-angiogenic activity, administration will may be by a route involving circulation of the liposomes in the bloodstream, including intravenous administration.

The liposomes may be administered in conventional dosage forms prepared by combining the liposomes with standard pharmaceutical carriers according to conventional procedures. The liposomes may also be administered in conventional dosages in combination with one or more other therapeutically active or diagnostic compounds. These procedures may involve mixing, granulating and compressing or dissolving the ingredients as appropriate to the desired preparation.

It will be appreciated that the form and character of the pharmaceutically acceptable carrier or diluent is dictated by the amount of liposome and other active agents with which it is to be combined, the route of administration and other well known variables. The carrier(s) must be "acceptable" in the sense of being compatible with the other ingredients of the formulation and not deleterious to the recipient thereof. The liposomes will typically be provided in suspension form in a liquid carrier such as aqueous saline or buffer. In general, the pharmaceutical form will comprise the liposomes in an amount sufficient to deliver the liposome or loaded compound in the desired dosage amount and regimen.

The liposomes are administered in an amount sufficient to deliver the liposome or loaded compound in the desired dosage according to the desired regimen, to ameliorate or prevent the disease state which is being treated, or to image the disease site being diagnosed or monitored.

It will be recognized by one of skill in the art that the optimal quantity and spacing of individual dosages of the liposomes will be determined by the nature and extent of the condition being treated, diagnosed or monitored, the form, route and site of administration, and the particular patient being treated, and that such optimums can be determined by conventional techniques. It will also be appreciated by one of skill in the art that the optimal course of treatment, i.e., the number of doses of the liposomes given per day for a defined number of days, can be ascertained by those skilled in the art using conventional course of treatment determination tests.

Once administered, the liposomes associate with the targeted tissue, or are carried by the circulatory system to the targeted tissue, where they associate with the tissue. At the targeted tissue site, the receptor antagonist may itself exhibit clinical efficacy, that is, the liposomes per se may be useful in treating disease presenting the targeted receptors. As will be appreciated by those skilled in the art, the selection of the liposome may be based on the expression of the conjugate's cognate receptor on of the patient's diseased cells, which can be determined by known methods or which may be based on historical information for the disease.

In addition or alternatively, the therapeutic or diagnostic agent associated with the liposomes is released or diffuses to the targeted tissue where it performs its intended function.

V. Methods of Preparation

EXAMPLE 1

Preparation of α-formyl-ω-hydroxyl polyethylene oxide-co-polyglycidol by Protected Aldehyde Method.

Synthesis of the polymer involves three two: polymerization using a protected aldehyde containing alcohol, and removing the protective group to yield the aldehyde.

a) THF 20 ml, 3,3-diethoxypropanol 0.15 g, and a potassium naphthalene 0.5 mol/L-tetrahydrofuran solution 2 ml are added to a reaction container and are agitated for 3 minutes in an argon atmosphere; a potassium compound of 3,3-diethoxypropanol (potassium 3,3-diethoxypropanoxide) will be produced.

b) A mixture of ethyleneoxide 8.8 g and glycidol is added to this solution mixture, and agitated at room temperature and 1 atm. After reacting for about 12 hours, the reaction mixture is poured into cold petroleum ether to precipitate the copolymer.

c) 2.0 mol/L-HCl 50 ml is added to THF 50 ml in which the copolymer sample of step b) is dissolved, and this mixture is agitated for about 1 hour at room temperature. After this solution is neutralized with a NaOH aqueous solution, four hours of dialysis (fractional molecular weight 1000) is performed against 20 times the amount of water and this is refined by freeze drying.

EXAMPLE 2

Preparation of α-carboxyl-ω-hydroxyl polyethylene oxide-co-polyglycidol.

Initiator: 4-hydroxy butyric acid-sodium/potassium salt (K/NaOCO—CH2CH2CH2OK/Na)

Synthesis of the polymer in one step:

a) Copolymerization of ethylene oxide and glycidol are carried out in a high pressure reactor (Par reactor) equipped with a magnetic driven mechanical stirrer. The reactor is bubbled with dried argon.

b) The initiator is prepared separately in a three necked 1 L flask equipped with magnetic stirrer and a condenser with three way stopcock. 4-hydroxy butyric acid-sodium salt (5.7 g 0.045 mol) (Fluka Chemical Co) is added to the flask followed by addition of freshly cut potassium (1.8 g 0.046 mol). After addition of the solid content the flask is evacuated followed by pressurizing (30 psi) with argon. Dried tetrahydrofuran (THF) 400 ml is added and the solution is refluxed for about 12 hours. A heterogeneous solution is formed. This solution is transferred to high pressure Par reactor under a flow of argon using 12 gauge double tip stainless steel needle. The reactor temperature is lowered to −10° C. Freshly distilled ethylene oxide (50 ml) (distilled over n-butyllithium) and glycidol (Aldrich Chemical Co) is added using stainless steel capillary. The solution is stirred at 50° C. for about 24 hours. The reactor temperature is allowed to cool to water bath temperature and the reactor content is poured into a glass beaker containing HCl (5 ml of 35% aqueous solution). A slight yellow colour solution is formed with the precipitation of salt (KCl). The solution is filtered and the filtrate is precipitated in cold 2-propanol containing 20% hexanes, giving the desired product as a light yellow precipitate, which is dried in a vacuum overnight.

c) In an Erlenmeyer flask equipped with a magnetic stir bar, the obtained polymer from the preceding step (step b) is added to 500 ml distilled deionized water, and stirred to dissolve, followed by addition of dichloromethane to extract the polymer and to remove the unreacted initiator and residual amount of salt present. The solution is washed with deionized water two times, than the dichloromethane solution is concentrated in rotavapor.

The molecular weight of the copolymer will be determined by size exclusion chromatography using THF as the mobile phase. The detection will be performed using a Dawn eighteen angle light scattering detector (Wyatt Technology Corporation).

The carboxylic content of the copolymer can be determined by acid-base titration using 0.02 N Sodium Hydroxide.

EXAMPLE 3

Preparation of an α-carboxylic ω-hydroxyl polyethylene oxide-co-polyglycidol

Initiator: 4-hydroxy butyric acid-sodium/potassium salt (K/NaOCO—CH2CH2CH2OK/Na)

a) Copolymerization of ethylene oxide and glycidol is carried out as outlined in example 2 above. An initiator based on potassium alcoholate of 4-hydroxy butyric acid sodium salt, and 4-hydroxy butyric acid (4.2 g 0.033 mol) is stirred in dried tetrahydrofuran (THF) 400 ml, and the solution is brought to 40° C. The solution is treated with potassium 1.3 g (0.033 mol) and the solution is refluxed for about 12 hours. A heterogeneous solution will be formed. This solution is transferred to high pressure Par reactor under a flow of argon using 12 gauge double tip stainless steel needle. The reactor temperature is lowered to −10° C. Freshly distilled ethylene oxide (80 ml 70 g) (distilled over n-butyl lithium) and glycidol are added using stainless steel capillary. The solution is stirred at 50° C. for about 24 hours. The reactor temperature is allowed to cool to water bath temperature and the reactor content is poured into a glass beaker containing HCl (5 ml of 35% aqueous solution). A slight yellow colour solution is formed with the precipitation of salt (KCl). The solution is filtered, and the filtrate precipitated, in cold 2-propanol containing 20% hexanes, giving the desired product as a light yellow precipitate, which is dried in vacuo overnight.

EXAMPLE 4

Preparation of an α-carboxylic ω-hydroxyl polyethylene oxide-co-polyglycidol a) Copolymerization of ethylene oxide and glycidol is carried out as outlined in example 2, above. Initiator is based on potassium alcoholate of 4 hydroxy butyric acid sodium salt, and 4-hydroxy butyric acid (4.2 g 0.033 mol) is stirred in dried tetrahydrofuran (THF) 400 ml, mixed with 18 crown ether 6 (8.7 g 0.033 mol) and potassium (1.3 g 0.033 mol) and the solution is brought to 40° C., and stirred. A deep violet blue colour is formed and will disappear simultaneously. Finally, a heterogeneous solution will be formed and the potassium metal will completely disappear.

b) The solution of part a) is transferred to high pressure par reactor under a flow of argon using 12 gauge double tip stainless steel needle. The reactor temperature is lowered to −10° C. Freshly distilled ethylene oxide (95 ml 83.6 g) (distilled over n-butyl lithium) is added using stainless steel capillary. The solution is stirred at 50° C. for about 24 hours. The reactor temperature is cooled to water bath temperature, and the reactor contents are poured into a glass beaker containing HCl (5 ml of 35% aqueous solution). A slight yellow colour solution is formed with the precipitation of salt (KCl). The solution is filtered and the filtrate is precipitated in cold 2-propanol containing 20% hexanes, giving the desired product as a light yellow precipitate, which is dried in vacuum overnight.

EXAMPLE 5

Preparation of an α-carboxylic ω-hydroxyl polyethylene oxide-co-polyglycidol (Formation of Hyperbranched Polyglyciol First and Subsequent Polymerization of Ethylene Oxide)

a) The initiator from example 2 above is prepared and transferred to high pressure Par reactor under a flow of argon using 12 gauge double tip stainless steel needle. The reactor temperature is lowered to −10° C. Glycidol in THF is slowly added using stainless steel capillary. The solution is stirred at 50° C. for about 12 hours. Then freshly distilled ethylene oxide (95 ml 83.6 g) (distilled over n-butyl lithium) is added using stainless steel capillary. The solution is stirred at 50° C. for about 24 hours. The reactor temperature is allowed to cool to water bath temperature, and the reactor contents are poured into a glass beaker containing HCl (5 ml of 35% aqueous solution). A slight yellow colour solution is formed with the precipitation of salt (KCl). The solution is filtered, and the filtrate precipitated in cold 2-propanol containing 20% hexanes, giving the desired product as a light yellow precipitate, which is dried in vacuum overnight.

EXAMPLE 6

Preparation of an α-carboxylic ω-hydroxyl polyethylene oxide-co-polyglycidol (Formation of Polyethylene Block First and Subsequent Polymerization of Polyglycidol)

a) The initiator from example 2, above, is prepared and transferred to high pressure Par reactor under a flow of argon using 12 gauge double tip stainless steel needle. The reactor temperature is lowered to −10° C. and freshly distilled ethylene oxide (95 ml 83.6 g) (distilled over n-butyl lithium) is added using stainless steel capillary. The solution is stirred at 50° C. for about 24 hours. Glycidol in THF is slowly added using stainless steel capillary. The solution is stirred at 50° C. for about 12 hours. The reactor temperature is allowed to cool to water bath temperature and the reactor content is poured into a glass beaker containing HCl (5 ml of 35% aqueous solution). A slight yellow colour solution is formed with the precipitation of salt (KCl). The solution is filtered and the filtrate precipitated in cold 2-propanol containing 20% hexanes, giving the desired product as a light yellow precipitate, which is dried in vacuo overnight.

EXAMPLE 7

Synthesis of an α-hydroxy-ω-succinimidyl-PEG-co-polyglycidol a) In a round bottom flask equipped with a magnetic stir bar and three way stop cock with a rubber septum, attached to a nitrogen line and a bubbler, the copolymer from example 6, (10.00 g; 0.011 mol), N,N'-dicyclohexyl carbodiimide (1.5 times excess; 3.64 g; 0.0176 mol) and N-hydroxysuccinimide (1.5 times; 2.03 g; 0.0176 mol) are dissolved in 150 ml dichloromethane. The flask is kept at room temperature and the solution stirred overnight. A cloudy heterogeneous white in colour will precipitate out. The reaction mixture is filtered, and the filtrate is concentrated under reduced pressure, filtered and precipitated into cold diethyl ether, and finally the resultant solution crystalizes from dried ethanol.

EXAMPLE 8

Conjugation of an α-hydroxy-ω-succinimidyl-PEG-co-polyglycidol to a Protein

Solid alpha hydroxy—omega succinimidyl—PEG-co-polyglycidol (obtained from example 7) is added to a 2.5 mg/mL solution of Grob-t in Dulbeccu's phosphate buffered (DPBS) pH 7.0. NHS-copolymer is added to the protein solution at molar ratio of NHS-copolymer to protein ration of 2:1, 4:1 or 10:1. The reaction is allowed to proceed at 40° C. for about 3 hours. At the end of the reaction, excess amounts of glycine (0.5M) are added to quench the reaction, and pH of the reaction mixture is adjusted to about pH 4.5 with 3N HCl. The title compound/product is purified by diafiltration.

EXAMPLE 9

Conjugation of an α-hydroxy-ω-succinimidyl-PEG-co-polyglycidol to a Lipid

A chloroform solution (10 ml) of N-hydroxysuccinimidyl copolymer (0.8 mmole) is added distearoyl phosphatidylethanolamine, DSPE (0.52 g, 0.70 mmole) containing triethylamine (0.2 ml, 1.4 mmole). The mixture is maintained in an oil bath heated to 40–45° C. for 2 hours. At the completion of the reaction, the title compound/product is isolated and purified by diafiltration.

EXAMPLE 10

Incorporation of Copolymer Conjugated Lipids Into Liposomes:

Liposomes comprising the copolymer-lipid conjugate of Example 9 are prepared as follows. The composition of the lipid materials is shown in Table 1, below.

TABLE 1

| Lipid Material | Examples | | | | | | | |
|---|---|---|---|---|---|---|---|---|
| (Mole %) | 10a | 10b | 10c | 10d | 10e | 10f | 10g | 10h |
| Copolymer-Lipid Conjugate | 1 | 5 | 10 | 20 | 1 | 5 | 10 | 20 |
| DSPC | 54 | 50 | 45 | 35 | 54 | 50 | 45 | 35 |
| Cholesterol | 45 | 45 | 45 | 45 | 45 | 45 | 45 | 45 |

The lipid materials are individually weighed and combined into an appropriately sized vessel. The lipids are completely dissolved in organic solvent, such as CHCl$_3$/MeOH 95/5 v/v, Benzene:MeOH 70/30 v/v, or ethanol. The solvent is evaporated off (or lyophilized in the case of benzene:methanol) and trace solvent is removed under high vacuum. The lipid film is resuspended in aqueous buffer containing 20 mM Hepes, 150 mM NaCl pH 7.4 (HBS) at 65 degrees Celsius with vortexing. The lipid suspension is sized by extrusion through 2–100 nm diameter polycarbonate filters to form 100 nm diameter vesicles.

Additional liposomes may be prepared from the components shown in Table 1 which reflect the target mol % composition and the target weights of each component employed.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound represented by the structure:

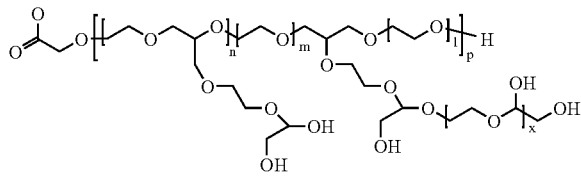

wherein
 l is an integer having the value of 0 to 10,000;
 m is an integer having the value of 0 to 10,000;
 n is an integer having the value of 1 to 100;
 p is an integer having the value of 1 to 100; and
 x is an integer having the value of 1 to 100.

2. A conjugate comprising the compound according to claim 1 with at least one agent selected from an active agent, a protein, a diagnostic agent, an imaging agent, and a polypeptide.

3. A delivery vehicle comprising at least one conjugate according to claim 2, wherein the vehicle delivers at least one agent selected from the active agent, protein, diagnostic agent, imaging agent, and polypeptide to a human in need thereof.

4. A conjugate comprising the compound according to claim 1 with at least one lipid.

5. A delivery vehicle comprising at least one conjugate according to claim 4, wherein the vehicle delivers a therapeutic active agent in an animal in need thereof.

6. A conjugate comprising the compound according to claim 1 with at least one hydrophobic polymer which results in an amphiphilic copolymer capable of forming a polymeric micelle.

7. A delivery vehicle comprising at least one conjugate according to claim 6, wherein the vehicle delivers a therapeutic active agent in an animal in need thereof.

8. A liposome comprising:
 a) at least one composition according to claim 1;
 b) at least one vesicle forming lipid;
 c) optionally at least one targeting moiety;
 d) and optionally at least one therapeutic active agent chosen from drugs, proteins, peptides, imaging agents, radioactive agents, and nucleic acids.

9. A compound represented by the structure:

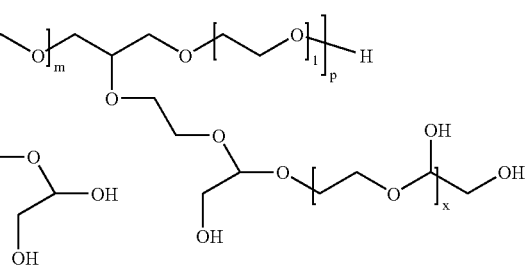

wherein
l is an integer having the value of 0 to 10,000;
m is an integer having the value of 0 to 10,000;
n is an integer having the value of 1 to 100;
p is an integer having the value of 1 to 100; and
x is an integer having the value of 1 to 100.

10. A conjugate comprising the compound according to claim 9 with at least one hydrophobic polymer which results in an amphiphilic copolymer capable of forming a polymeric micelle.

11. A conjugate comprising the compound according to claim 9 with at least one agent selected from an active agent, a protein, a diagnostic agent, an imaging agent, a lipid, and a polypeptide.

12. A delivery vehicle comprising at least one conjugate according to claim 11, wherein the vehicle delivers a therapeutic active agent in an animal in need thereof.

13. A compound represented by the structure:

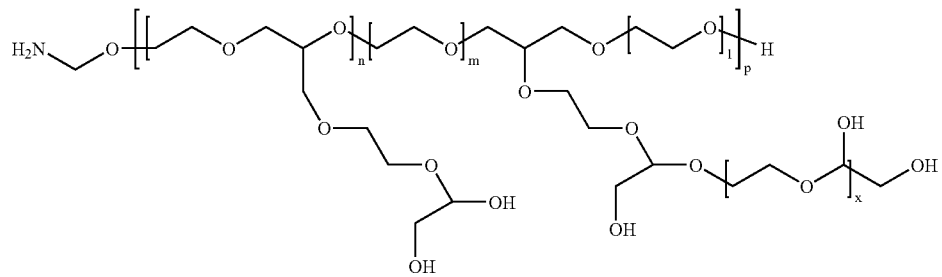

wherein
l is an integer having the value of 0 to 10,000;
m is an integer having the value of 0 to 10,000;
n is an integer having the value of 1 to 100;
p is an integer having the value of 1 to 100; and
x is an integer having the value of 1 to 100.

14. A conjugate comprising the compound according to claim 13 with at least one agent selected from an active agent, a protein, a diagnostic agent, an imaging agent, a lipid, and a polypeptide.

15. A delivery vehicle comprising at least one conjugate according to claim 14, wherein the vehicle delivers a therapeutic active agent in an animal in need thereof.

16. A conjugate comprising the compound according to claim 13 with at least one hydrophobic polymer which results in an amphiphilic copolymer capable of forming a polymeric micelle.

17. A compound represented by the structure:

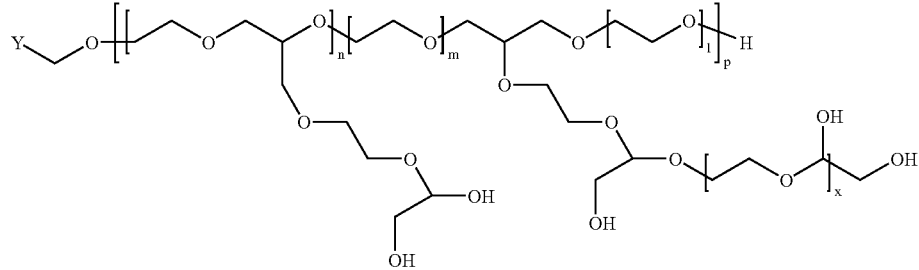

wherein
Y is an active agent, a hydrophobic polymer, or a lipid;
l is an integer having the value of 0 to 10,000;
m is an integer having the value of 0 to 10,000;
n is an integer having the value of 1 to 100;
p is an integer having the value of 1 to 100; and
x is an integer having the value of 1 to 100.

18. A compound represented by the structure:

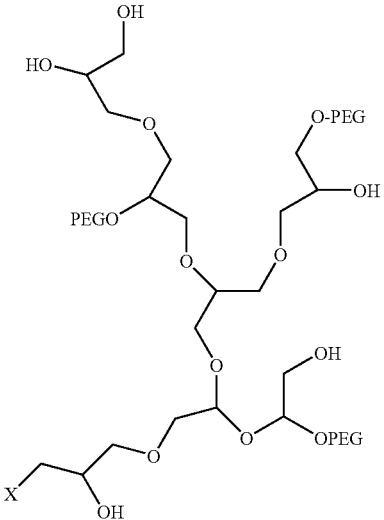

wherein
X is NH2, COOH, CHO, or modifications thereof; and
PEG is a repeating unit of polyethylene glycol having a molecular weight from about 500 to about 20,000 mw.

19. A conjugate comprising the compound according to claim 18 with at least one agent selected from an active agent, a protein, a diagnostic agent, an imaging agent, a lipid, and a polypeptide.

20. A delivery vehicle comprising at least one conjugate according to claim 19 wherein the vehicle delivers a therapeutic active agent in an animal in need thereof.

21. A conjugate comprising the compound according to claim 18 with at least one hydrophobic polymer which results in an amphiphilic copolymer capable of forming a polymeric micelle.

22. A compound represented by the structure:

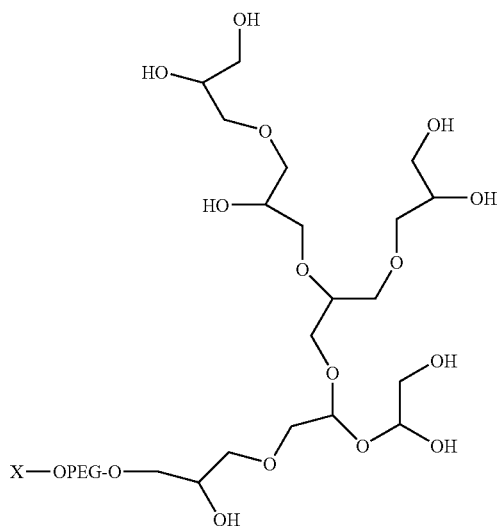

wherein
X is NH2, COOH, COGH or modifications thereof; and
PEG is a repeating unit of polyethylene glycol having a molecular weight from about 500 to about 20,000 mw.

23. A conjugate comprising the compound according to claim 22 with at least one agent selected from an active agent, a protein, a diagnostic agent, an imaging agent, a lipid, and a polypeptide.

24. A conjugate comprising the compound according to claim 22 with at least one hydrophobic polymer which results in an amphiphilic copolymer capable of forming a polymeric micelle.

25. A process of making a derivatized heterofunctional random architecture hyperbranched copolymer comprising
i) adjusting the ratio of the monomers glycidol and ethylene oxide to each other in the polymerization medium; to
ii) adding to the polymerization medium a polymerization initiator having a protected heterofunctionality and a free hydroxyl group; and
iii) producing a copolymer having two different functional groups at the termini of the resulting hyperbranched copolymer of polyethylene oxide and polyglycidol; and
iv) deprotecting the heterofunctionality as necessary or desired.

26. The process according to claim 25 wherein one of the functional termini groups is a carboxylic group which may be converted to any suitable or desired reactive species.

27. The process according to claim 25 wherein one of the functional termini groups upon deprotection yields an amino group.

28. The process according to claim 25 wherein one of the functional termini groups upon deprotection yields an aldehyde.

29. The process according to claim 25 wherein one of the functional termini groups upon deprotection yields a carboxylic acid.

30. The process according to claim 25 wherein the protected heterofunctionality of the polymerization initiator is a protected amine, a protected aldehyde or a protected carboxylic acid.

31. The process according to claim 25 wherein the protected heterofunctionality of the polymerization initiator is a protected amine.

32. The process according to claim 25 wherein the initiator contains both an unprotected and a protected amine functionality.

33. The process according to claim 25 wherein the derivatized heterofunctional random architecture hyperbranched copolymer is further reacted to form a conjugate with at least one agent selected from an active agent, a protein, a diagnostic agent, an imaging agent, a lipid, and a polypeptide.

34. A process of making a derivatized heterofunctional random architecture hyperbranched copolymer comprising
i) adjusting the order of addition of the monomers glycidol and ethylene oxide to each other as they are added to a polymerization medium;

ii) adding to the polymerization medium a polymerization initiator having a protected heterofunctionality and a free hydroxyl group; and iii) producing a copolymer having two different functional groups at the termini of the resulting hyperbranched copolymer of polyethylene oxide and polyglycidol; and iv) deprotecting the heterofunctionality as necessary or desired.

35. The process according to claim 34 wherein one of the functional termini groups is a carboxylic group which may be converted to any suitable or desired reactive species.

36. The process according to claim 34 wherein one of the functional termini groups upon deprotection yields an amino group.

37. The process according to claim 34 wherein one of the functional termini groups upon deprotection yields an aldehyde.

38. The process according to claim 34 wherein one of the functional termini groups upon deprotection yields a carboxylic acid.

39. The process according to claim 34 wherein the protected heterofunctionality of the polymerization initiator is a protected amine, a protected aldehyde or a protected carboxylic acid.

40. The process according to claim 34 wherein the protected heterofunctionality of the polymerization initiator is a protected amine.

41. The process according to claim 34 wherein the initiator contains both an unprotected and a protected amine functionality.

42. The process according to claim 34 wherein the derivatized heterofunctional random architecture hyperbranched copolymer is further reacted to form a conjugate with at least one agent selected from an active agent, a protein, a diagnostic agent, an imaging agent, a lipid, and a polypeptide.

43. A process of making a derivatized heterofunctional random architecture hyperbranched copolymer comprising i) adjusting the rate of addition of the monomers glycidol and ethylene oxide to each other as they are added to a polymerization medium;

ii) adding to a polymerization medium a polymerization initiator having a protected heterofunctionality and a hydroxyl linkage; and ii) producing a copolymer having two different functional groups at the termini of the resulting hyperbranched copolymer of polyethylene oxide and polyglycidol; and iv) deprotecting the heterofunctionality as necessary or desired.

44. The process according to claim 43 wherein one of the functional termini groups is a carboxylic group which may be converted to any suitable or desired reactive species.

45. The process according to claim 43 wherein one of the functional termini groups upon deprotection yields an amino group.

46. The process according to claim 43 wherein one of the functional termini groups upon deprotection yields an aldehyde.

47. The process according to claim 43 wherein one of the functional termini groups upon deprotection yields a carboxylic acid.

48. The process according to claim 43 wherein the protected heterofunctionality of the polymerization initiator is a protected amine, a protected aldehyde or a protected carboxylic acid.

49. The process according to claim 43 wherein the protected heterofunctionality of the polymerization initiator is a protected amine.

50. The process according to claim 43 wherein the initiator contains both an unprotected and a protected amine functionality.

51. The process according to claim 43 wherein the derivatized heterofunctional random architecture hyperbranched copolymer is further reacted to form a conjugate with at least one agent selected from an active agent, a protein, a diagnostic agent, an imaging agent, a lipid, and a polypeptide.

* * * * *